United States Patent
Honold et al.

(10) Patent No.: US 8,058,283 B2
(45) Date of Patent: Nov. 15, 2011

(54) 7H-PYRIDO[3,4-D]PYRIMIDIN-8-ONES, THEIR MANUFACTURE AND USE AS PROTEIN KINASE INHIBITORS

(75) Inventors: Konrad Honold, Penzberg (DE); Jane Paul, Camelford/Cornwall (GB); Carl Roeschlaub, Bude/Cornwall (GB); Wolfgang Schaefer, Mannheim (DE); Stefan Scheiblich, Penzberg (DE); Thomas Von Hirschheydt, Penzberg (DE); Alan Whittle, Bridgerule/Devon (GB)

(73) Assignee: Hoffmann-La Roche Inc., Nutley, NJ (US)

( * ) Notice: Subject to any disclaimer, the term of this patent is extended or adjusted under 35 U.S.C. 154(b) by 805 days.

(21) Appl. No.: 12/087,420

(22) PCT Filed: Jan. 29, 2007

(86) PCT No.: PCT/EP2007/000725
§ 371 (c)(1), (2), (4) Date: Jul. 1, 2008

(87) PCT Pub. No.: WO2007/088014
PCT Pub. Date: Aug. 9, 2007

(65) Prior Publication Data
US 2009/0030020 A1    Jan. 29, 2009

(30) Foreign Application Priority Data
Jan. 31, 2006   (EP) .................................... 06001915

(51) Int. Cl.
| C07D 471/04 | (2006.01) |
| A61K 31/519 | (2006.01) |
| A61P 29/00 | (2006.01) |
| A61P 35/00 | (2006.01) |
| A61P 5/22 | (2006.01) |
| A61P 37/00 | (2006.01) |
| A61P 25/00 | (2006.01) |

(52) U.S. Cl. ................................. 514/264.11; 544/279
(58) Field of Classification Search ............. 514/264.11; 544/279
See application file for complete search history.

(56) References Cited

FOREIGN PATENT DOCUMENTS

| WO | WO 96/15128 | 5/1996 |
| WO | WO 96/34867 | 11/1996 |
| WO | WO 99/61444 | 12/1999 |
| WO | WO 00/24744 | 5/2000 |
| WO | WO 01/29041 | 4/2001 |
| WO | WO 01/29042 | 4/2001 |
| WO | WO 02/18379 | 3/2002 |
| WO | WO 02/18380 | 3/2002 |
| WO | WO 2004/011465 | 2/2004 |
| WO | WO 2004/041821 | 5/2004 |
| WO | WO 2004/041823 | 5/2004 |
| WO | WO 2004/075852 | 9/2004 |
| WO | WO 2004/089955 | 10/2004 |
| WO | WO 2005/011597 | 2/2005 |
| WO | WO 2005/034869 | 4/2005 |
| WO | WO 2007/088014 | 8/2007 |

OTHER PUBLICATIONS

Trumpp-Kallmeyer S. et al., J. Med. Chem. vol. 41 (1998) pp. 1752-1763.
Klutchko, S. R. et al., J. Med. Chem. vol. 41 (1998) pp. 3276-3292.

*Primary Examiner* — James O Wilson
*Assistant Examiner* — Cecilia M Jaisle
(74) *Attorney, Agent, or Firm* — George W. Johnston; Patricia S. Rocha-Tramaloni; Gene J. Yao

(57) ABSTRACT

Objects of the present invention are the compounds of formula I

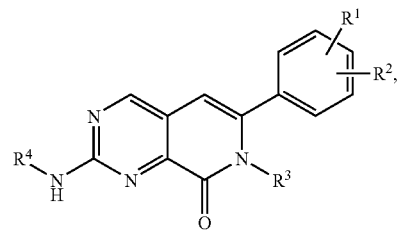

formula I their pharmaceutically acceptable salts, enantiomeric forms, diastereoisomers and racemates, the preparation of the above compounds, medicaments containing them and their manufacture, as well as the use of the above compounds in the control or prevention of illnesses such as cancer.

6 Claims, No Drawings

7H-PYRIDO[3,4-D]PYRIMIDIN-8-ONES, THEIR MANUFACTURE AND USE AS PROTEIN KINASE INHIBITORS

PRIORITY TO RELATED APPLICATION

This application claims the benefit of European Patent Application No. 06001915.5, filed Jan. 31, 2006, which is hereby incorporated by reference in its entirety.

The present invention relates to novel 7H-pyrido[3,4-d]pyrimidin-8-one derivatives, to a process for their manufacture, pharmaceutical compositions containing them and their manufacture as well as the use of these compounds as pharmaceutically active agents.

BACKGROUND OF THE INVENTION

Protein kinases are enzymes that catalyze the transfer of a phosphate group from ATP to an amino acid residue, such as tyrosine, serine, threonine, or histidine on a protein. Regulation of these protein kinases is essential for the control of a wide variety of cellular events including proliferation and migration.

Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489-495; Biscardi, J. S., et al., Adv. Cancer Res. 76 (2000) 61-119.

The tyrosine kinases are a class of protein kinases. The Src family which consists of at least eight members (Src, Fyn, Lyn, Yes, Lck, Fgr, Hck and Blk) that participate in a variety of signaling pathways represents the major family of cytoplasmic protein tyrosine kinases (Schwartzberg, P. L., Oncogene 17 (1998) 1463-1468). The prototypical member of this tyrosine kinase family is Src, which is involved in proliferation and migration responses in many cell types (Sawyer, T., et al., Expert Opin. Investig. Drugs 10 (2001) 1327-1344). Src activity has been shown to be elevated in different cancers, e.g. breast, colon (>90%), pancreatic (>90%) and liver (>90%) tumors. Highly increased Src activity is also associated with metastasis (>90%) and poor prognosis. Antisense Src message impedes growth of colon tumor cells in nude mice (Staley, C. A., Cell Growth Differ. 8 (1997) 269-274), suggesting that Src inhibitors could slow tumor growth. Furthermore, in addition to its role in cell proliferation, Src also acts in stress response pathways, including the hypoxia response. Nude mice studies with colon tumor cells expressing antisense Src message have reduced vascularization (Ellis, L. M., et al., J. Biol. Chem. 273 (1998) 1052-1057), which suggests that Src inhibitors could be anti-angiogenic as well as anti-proliferative.

Src disrupts E-cadherin associated cell-cell interactions (Avizienyte, E., et al., Nature Cell Bio. 4 (2002) 632-638). A low molecular weight Src inhibitor prevents this disruption thereby reducing cancer cell metastasis (Nam, J. S., et al., Clin. Cancer Res. 8 (2002) 2430-2436).

Src inhibitors may prevent the secondary injury that results from a VEGF-mediated increase in vascular permeability such as that seen following stroke (Eliceiri, B. P., et al., Mol. Cell. 4 (1999) 915-924; Paul, R., et al., Nat. Med. 7 (2001) 222-227).

Blockade of Src prevents dissociation of the complex involving Flk, VE-cadherin, and β-catenin with the same kinetics with which it prevents VEGF-mediated VP/edema and account for the Src requirement in VEGF-mediated permeability and provide a basis for Src inhibition as a therapeutic option for patients with acute myocardial infarction (Weis, S., et al., J. Clin. Invest. 113 (2004) 885-894).

Src also plays a role in osteoporosis. Mice genetically engineered to be deficient in Src production were found to exhibit osteopetrosis, the failure to resorb bone (Soriano, P., et al., Cell 64 (1991) 693-702; Boyce, B. F., et al., J. Clin., Invest. 90 (1992) 1622-1627). This defect was characterized by a lack of osteoclast activity. Since osteoclasts normally express high levels of Src, inhibition of Src kinase activity may be useful in the treatment of osteoporosis (Missbach, M., et al., Bone 24 (1999) 437-449).

Low molecular weight inhibitors for protein kinases are widely known in the state of the art. For the inhibition of src and other kinases such inhibitors are based on i.e. 8H-pyrido[2,3-d]pyrimidin-7-one derivatives (see e.g. WO 96/34867, WO 96/15128, U.S. Pat. No. 5,733,914, WO 02/018379, WO 02/018380, WO 2005/034869, Klutchko, S. R, et al., J. Med. Chem. 41 (1998) 3276-3292 or Blankley, C. J., J. Med. Chem. 41 (1998) 1752-1763) or 3,4-dihydro-1H-pyrimido[4,5-d]pyrimidin-2-one derivatives (see e.g. WO 99/61444, WO 00/024744, WO 01/029041, WO 01/029042, WO 2004/011465, WO 2004/041821, WO 2004/041823, WO 2004/075852, WO 2004/089955 or WO 2005/011597). Some pyrido-pyrimidinone derivatives are known from cross-coupling reaction studies (Sakamoto, T., et al., Chemical & Pharmaceutical Bulletin 30 (1982) 2410-2416).

SUMMARY OF THE INVENTION

The present invention relates to 7H-pyrido[3,4-d]pyrimidin-8-one derivatives of the general formula I

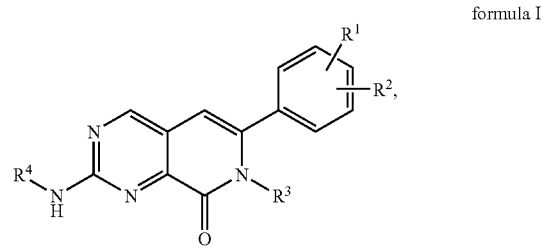

formula I wherein $R^1$ is halogen, alkyl, alkoxy, halogenated alkyl or halogenated alkoxy;

$R^2$ is hydrogen, halogen, alkyl, alkoxy, halogenated alkyl or halogenated alkoxy;

$R^3$ is alkyl which is optionally substituted one or several times with cyano, —OR, —NRR', —C(O)NRR', —NR—C(O)-alkyl, —S(O)$_2$NRR', —NR—S(O)$_2$-alkyl, heteroaryl, heterocyclyl, unsubstituted phenyl or phenyl substituted one or several times with halogen, alkyl, alkoxy or cyano;

$R^4$ is a) alkyl wherein the alkyl is optionally substituted one or several times with —OR or —NRR';
  b) phenyl wherein the phenyl is optionally substituted one or several times with alkyl, alkoxy, heterocyclyl, —C(O)NRR', —NR—C(O)-alkyl, —S(O)-alkyl, —S(O)$_2$NR-alkyl or —NR—S(O)$_2$-alkyl, and wherein all alkyl and alkoxy groups are optionally substituted one or several times with —OR or —NRR'; or
  c) heterocyclyl;

R and R' are hydrogen or alkyl;
and all pharmaceutically acceptable salts thereof.

The compounds according to this invention show activity as protein kinase inhibitors, in particular as src family tyrosine kinase inhibitors (especially as src and lck inhibitors) and furthermore as inhibitors of Abl, PDGFR, Raf tyrosine kinase inhibitors, and may therefore be useful for the treatment of diseases mediated by said tyrosine kinases.

The family of tyrosine kinases plays an important role in the regulation of cell signaling and cell proliferation by phosphorylating tyrosine residues of peptides and proteins. Inappropriate activation of tyrosine kinases is known to be involved in a variety of disease states including inflammatory, immunological, CNS disorders, or oncological disorders, or bone diseases. See for example Susva, M., et al., Trends Pharmacol. Sci. 21 (2000) 489-495; Biscardi, J. S., et al., Adv. Cancer Res. 76 (2000) 61-119.

Src, Abl, PDGFR and Raf kinase inhibition exerts an antiproliferative effect in tumor cell lines. This indicates that Src, Abl, PDGFR and Raf kinase inhibitors may be useful in the treatment of i.e. hyperproliferative diseases such as cancer and in particular colorectal, breast, lung, prostate, pancreatic, gastric, bladder, ovarian, melanoma, neuroblastoma, cervical, kidney or renal cancers, leukemias or lymphomas.

Src family kinases are further known to be involved in a variety of other disease states. Compounds of the present invention may be further used as Src family kinase inhibitors, especially as Src kinase inhibitors, in the prevention and therapy of, for example, transplant rejection, inflammatory bowel syndrome, rheumatoid arthritis, psoriasis, restenosis, allergic asthma, Alzheimer's disease, Parkinson, stroke, osteoporosis and benign.

Abl family kinases are further known to be involved in a variety of other disease states. Compounds of the present invention may be further used as Abl family kinase inhibitors, especially as Abl kinase inhibitors, in the prevention and therapy of, for example, neurodegenerative disease, rheumatoid arthritis and diabetes, including type I or type II diabetes.

PDGFR family kinases are further known to be involved in a variety of other disease states. Compounds of the present invention may be further used as PDGFR family kinase inhibitors, especially as PDGFR kinase inhibitors, in the prevention and therapy of, for example, diabetes, including type I or type II diabetes, restenosis (e.g. balloon injury induced restenosis), atherosclerosis or pulmonary fibrosis.

Objects of the present invention are the compounds of formula I and their tautomers, pharmaceutically acceptable salts, enantiomeric forms, diastereoisomers and racemates, their use for the inhibition of tumor growth, the preparation of the above-mentioned compounds, medicaments containing them and their manufacture as well as the use of the above-mentioned compounds in the control or prevention of illnesses, especially of cancers such as colorectal, breast, lung, prostate, pancreatic, gastric, bladder, ovarian, melanoma, neuroblastoma, cervical, kidney or renal cancers, leukemias or lymphomas, or in the manufacture of corresponding medicaments.

DETAILED DESCRIPTION OF THE INVENTION

1. Definitions

The term "halogen" means fluorine, chlorine or bromine, preferably fluorine or chlorine and especially chlorine.

The term "alkyl" as used herein means a saturated, straight-chain or branched-chain hydrocarbon containing from 1 to 4, preferably 1 to 3, carbon atoms. Examples of such alkyl groups include as methyl, ethyl, n-propyl, isopropyl, n-butyl, 2-butyl and t-butyl, preferably methyl.

The term "alkoxy" as used herein means an alkyl-O— group wherein the alkyl is defined as above. Examples of such alkoxy groups include as methoxy, ethoxy, n-propoxy and isopropoxy, preferably methoxy.

The term "halogenated alkyl" as used herein means an alkyl group as defined above which is substituted one or several times, preferably one to six and especially one to three times, by halogen, preferably by fluorine or chlorine, especially by fluorine. Examples are difluoromethyl, trifluoromethyl, 2,2,2-trifluoroethyl, perfluoroethyl, and the like, especially trifluoromethyl.

The term "halogenated alkoxy" as used herein means an alkoxy group as defined above which is substituted one or several times by halogen, preferably by fluorine or chlorine, especially fluorine. Examples are difluoromethoxy, trifluoromethoxy, 2,2,2-trifluoroethoxy, perfluoroethoxy and the like, especially trifluoromethoxy.

The term "heteroaryl" means a mono- or bicyclic aromatic ring with 5 to 10, preferably 5 to 6, ring atoms, which contains up to 3, preferably 1 or 2 heteroatoms selected independently from N, O or S and the remaining ring atoms being carbon atoms. Such heteroaryl groups can be optionally substituted one to three, preferably one or two times by alkyl, preferably by methyl. Examples of such heteroaryl groups include pyrrolyl, imidazolyl, pyrazolyl, methylpyrazolyl, dimethylpyrazolyl, triazolyl, tetrazolyl, furanyl, oxazolyl, isoxazolyl, thienyl, methylthienyl, thiazolyl, methylthiazolyl, pyridyl, pyrimidyl, pyridazinyl, pyrazinyl, indolyl, indazolyl, benzimidazolyl, benzothiophenyl, benzofuranyl, quinolyl, isoquinolyl, quinazolinyl and the like, preferably pyrazolyl, methylpyrazolyl or dimethylpyrazolyl, and especially dimethylpyrazolyl.

The term "heterocyclyl" means a saturated, monocyclic hydrocarbon ring with 5 to 6 ring atoms which contains up to 3, preferably 1 or 2 heteroatoms selected independently from N, O or S and the remaining ring atoms being carbon atoms. Such saturated heterocyclic group can be optionally substituted one to three, preferably one or two times by alkyl, preferably by methyl. Examples of such saturated heterocyclic groups are tetrahydrofuranyl, tetrahydropyranyl, morpholinyl, piperazinyl, N-methyl-piperazinyl, piperidyl, pyrrolidinyl, and the like, preferably tetrahydrofuranyl, tetrahydropyranyl, morpholinyl or N-methyl-piperazinyl.

As used herein, the term "a therapeutically effective amount" of a compound means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

2. Detailed Description $R^1$ is halogen, alkyl, alkoxy, halogenated alkyl or halogenated alkoxy, preferably halogen, alkyl or alkoxy, and more preferably halogen or alkyl.

$R^2$ is hydrogen, halogen, alkyl, alkoxy, halogenated alkyl or halogenated alkoxy, preferably hydrogen.

$R^3$ is alkyl which is optionally substituted one or several times, preferably one or two times, with cyano, —OR, —NRR', —C(O)NRR', —NR—C(O)-alkyl, —S(O)$_2$NRR', —NR—S(O)$_2$-alkyl, heteroaryl, heterocyclyl, unsubstituted phenyl or phenyl substituted one or several times, preferably one or two times, with halogen, alkyl, alkoxy or cyano. If the alkyl in the definition of $R^3$ is substituted, it is preferably substituted with —OR, —C(O)NRR', heteroaryl (preferably dimethylpyrazolyl), heterocyclyl (preferably tetrahydrofuranyl) or phenyl substituted one or two times with alkoxy.

$R^4$ is a) alkyl wherein the alkyl is optionally substituted one or several times, preferably one or two times, with —OR or —NRR'; b) phenyl wherein the phenyl is optionally substituted one or several times, preferably one or two times, with alkyl, alkoxy, heterocyclyl (preferably morpholinyl or N-methyl-piperazinyl), —C(O)NRR', —NR—C(O)-alkyl, —S(O)-alkyl, —S(O)$_2$NR-alkyl or —NR—S(O)$_2$-alkyl, preferably with alkyl, alkoxy, heterocyclyl, —S(O)-alkyl or —S(O)$_2$NR-alkyl, and wherein all alkyl and alkoxy groups, preferably the alkyl, alkoxy or —S(O)$_2$NR-alkyl group, are optionally substituted one or several times, preferably one or two times, with —OR or —NRR'; or c) heterocyclyl, preferably tetrahydrofuranyl.

R and R' are hydrogen or alkyl.

An embodiment of the invention are the compounds of formula I, wherein
- $R^1$ is halogen or alkyl;
- $R^2$ is hydrogen;
- $R^3$ is alkyl which is optionally substituted one or several times with —OR, —C(O)NRR', heteroaryl, heterocyclyl, unsubstituted phenyl or phenyl substituted one or several times with alkoxy; and
- $R^4$ is a) alkyl wherein the alkyl is optionally substituted one or several times with —OR or —NRR';
  b) phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'; or
  c) heterocyclyl.

Another embodiment of the invention are the compounds of formula I, wherein
- $R^1$ is halogen.

Another embodiment of the invention are the compounds of formula I, wherein
- $R^1$ is alkyl.

Another embodiment of the invention are the compounds of formula I, wherein
- $R^4$ is a) alkyl wherein the alkyl is optionally substituted one or several times with —OR or —NRR'; or b) heterocyclyl.

Another embodiment of the invention are the compounds of formula I, wherein
- $R^4$ is alkyl wherein the alkyl is optionally substituted one or several times with —OR or —NRR'.

Another embodiment of the invention are the compounds of formula I, wherein
- $R^1$ is halogen or alkyl;
- $R^2$ is hydrogen;
- $R^3$ is alkyl which is optionally substituted one or several times with —OR, —C(O)NRR', heteroaryl, heterocyclyl, unsubstituted phenyl or phenyl substituted one or several times with alkoxy; and
- $R^4$ is alkyl wherein the alkyl is optionally substituted one or several times with —OR or —NRR'.

Such compounds, for example, may be selected from the group consisting of:
2-(2-Hydroxy-1-hydroxymethyl-ethylamino)-7-methyl-6-o-tolyl-7H-pyrido[3,4-d]pyrimidin-8-one;
7-(1,5-Dimethyl-1H-pyrazol-3-ylmethyl)-2-(2-hydroxy-1-hydroxymethyl-ethylamino)-6-o-tolyl-7H-pyrido[3,4-d]pyrimidin-8-one; and
3-[6-(2-Chloro-phenyl)-2-(2-hydroxy-1-hydroxymethyl-ethylamino)-8-oxo-8H-pyrido[3,4-d]pyrimidin-7-yl]-propionamide.

Another embodiment of the invention are the compounds of formula I, wherein
- $R^4$ is phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'.

Another embodiment of the invention are the compounds of formula I, wherein
- $R^1$ is halogen or alkyl;
- $R^2$ is hydrogen;
- $R^3$ is alkyl which is optionally substituted one or several times with —OR, —C(O)NRR', heteroaryl, heterocyclyl, unsubstituted phenyl or phenyl substituted one or several times with alkoxy; and
- $R^4$ is phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'.

Such compounds, for example, may be selected from the group consisting of:
7-Methyl-2-(4-morpholin-4-yl-phenylamino)-6-o-tolyl-7H-pyrido[3,4-d]pyrimidin-8-one;
2-(3-Hydroxymethyl-phenylamino)-7-methyl-6-o-tolyl-7H-pyrido[3,4-d]pyrimidin-8-one;
7-Methyl-2-[4-(4-methyl-piperazin-1-yl)-phenylamino]-6-o-tolyl-7H-pyrido[3,4-d]pyrimidin-8-one;
2-{2-[4-(2-Hydroxy-ethylsulfamoyl)-phenylamino]-8-oxo-6-o-tolyl-8H-pyrido[3,4-d]pyrimidin-7-yl}-acetamide;
N-(2-Hydroxy-ethyl)-4-(7-methyl-8-oxo-6-o-tolyl-7,8-dihydro-pyrido[3,4-d]pyrimidin-2-ylamino)-benzenesulfonamide;
2-[4-(2-Diethylamino-ethoxy)-phenylamino]-7-methyl-6-o-tolyl-7H-pyrido[3,4-d]pyrimidin-8-one;
2-[2-(3-Methanesulfinyl-phenylamino)-8-oxo-6-o-tolyl-8H-pyrido[3,4-d]pyrimidin-7-yl]-acetamide;
2-(3-Methanesulfinyl-phenylamino)-7-methyl-6-o-tolyl-7H-pyrido[3,4-d]pyrimidin-8-one;
7-(1,5-Dimethyl-1H-pyrazol-3-ylmethyl)-2-(4-morpholin-4-yl-phenylamino)-6-o-tolyl-7H-pyrido[3,4-d]pyrimidin-8-one;
7-(3-Hydroxy-propyl)-2-[4-(4-methyl-piperazin-1-yl)-phenylamino]-6-o-tolyl-7H-pyrido[3,4-d]pyrimidin-8-one;
N-(2-Hydroxy-ethyl)-4-[7-(3-hydroxy-propyl)-8-oxo-6-o-tolyl-7,8-dihydro-pyrido[3,4-d]pyrimidin-2-ylamino]-benzenesulfonamide;
2-[4-(2-Diethylamino-ethoxy)-phenylamino]-7-(3-hydroxy-propyl)-6-o-tolyl-7H-pyrido[3,4-d]pyrimidin-8-one;
7-(3-Hydroxy-propyl)-2-(3-methanesulfinyl-phenylamino)-6-o-tolyl-7H-pyrido[3,4-d]pyrimidin-8-one;

7-(3-Methoxy-benzyl)-2-[4-(4-methyl-piperazin-1-yl)-phenylamino]-6-o-tolyl-7H-pyrido[3,4-d]pyrimidin-8-one;

N-(2-Hydroxy-ethyl)-4-[7-(3-methoxy-benzyl)-8-oxo-6-o-tolyl-7,8-dihydro-pyrido[3,4-d]pyrimidin-2-ylamino]-benzenesulfonamide;

2-[4-(2-Diethylamino-ethoxy)-phenylamino]-7-(3-methoxy-benzyl)-6-o-tolyl-7H-pyrido[3,4-d]pyrimidin-8-one;

2-(3-Methanesulfinyl-phenylamino)-7-(3-methoxy-benzyl)-6-o-tolyl-7H-pyrido[3,4-d]pyrimidin-8-one;

3-[2-(3-Hydroxymethyl-phenylamino)-8-oxo-6-o-tolyl-8H-pyrido[3,4-d]pyrimidin-7-yl]-propionamide;

3-{2-[4-(2-Hydroxy-ethylsulfamoyl)-phenylamino]-8-oxo-6-o-tolyl-8H-pyrido[3,4-d]pyrimidin-7-yl}-propionamide;

3-[2-(3-Methanesulfinyl-phenylamino)-8-oxo-6-o-tolyl-8H-pyrido[3,4-d]pyrimidin-7-yl]-propionamide;

6-(2-Chloro-phenyl)-7-(1,5-dimethyl-1H-pyrazol-3-ylmethyl)-2-[4-(4-methyl-piperazin-1-yl)-phenylamino]-7H-pyrido[3,4-d]pyrimidin-8-one;

6-(2-Chloro-phenyl)-2-[4-(2-diethylamino-ethoxy)-phenylamino]-7-(1,5-dimethyl-1H-pyrazol-3-ylmethyl)-7H-pyrido[3,4-d]pyrimidin-8-one;

6-(2-Chloro-phenyl)-7-(1,5-dimethyl-1H-pyrazol-3-ylmethyl)-2-(3-methanesulfinyl-phenylamino)-7H-pyrido[3,4-d]pyrimidin-8-one;

6-(2-Chloro-phenyl)-7-(3-hydroxy-propyl)-2-[4-(4-methyl-piperazin-1-yl)-phenylamino]-7H-pyrido[3,4-d]pyrimidin-8-one;

6-(2-Chloro-phenyl)-7-(3-methoxy-benzyl)-2-[4-(4-methyl-piperazin-1-yl)-phenylamino]-7H-pyrido[3,4-d]pyrimidin-8-one;

4-[6-(2-Chloro-phenyl)-7-(3-methoxy-benzyl)-8-oxo-7,8-dihydro-pyrido[3,4-d]pyrimidin-2-ylamino]-N-(2-hydroxy-ethyl)-benzenesulfonamide;

6-(2-Chloro-phenyl)-2-[4-(2-diethylamino-ethoxy)-phenylamino]-7-(3-methoxy-benzyl)-7H-pyrido[3,4-d]pyrimidin-8-one;

6-(2-Chloro-phenyl)-2-(3-methanesulfinyl-phenylamino)-7-(3-methoxy-benzyl)-7H-pyrido[3,4-d]pyrimidin-8-one;

6-(2-Chloro-phenyl)-2-(3-hydroxymethyl-phenylamino)-7-(tetrahydro-furan-2-ylmethyl)-7H-pyrido[3,4-d]pyrimidin-8-one;

6-(2-Chloro-phenyl)-2-[4-(4-methyl-piperazin-1-yl)-phenylamino]-7-(tetrahydro-furan-2-ylmethyl)-7H-pyrido[3,4-d]pyrimidin-8-one;

4-[6-(2-Chloro-phenyl)-8-oxo-7-(tetrahydro-furan-2-ylmethyl)-7,8-dihydro-pyrido[3,4-d]pyrimidin-2-ylamino]-N-(2-hydroxy-ethyl)-benzenesulfonamide;

6-(2-Chloro-phenyl)-2-[4-(2-diethylamino-ethoxy)-phenylamino]-7-(tetrahydro-furan-2-ylmethyl)-7H-pyrido[3,4-d]pyrimidin-8-one; and 6-(2-Chloro-phenyl)-2-(3-methanesulfinyl-phenylamino)-7-(tetrahydro-furan-2-ylmethyl)-7H-pyrido[3,4-d]pyrimidin-8-one.

Another embodiment of the invention are the compounds of formula I, wherein

R$^4$ is heterocyclyl.

Another embodiment of the invention are the compounds of formula I, wherein

R$^1$ is halogen or alkyl;

R$^2$ is hydrogen;

R$^3$ is alkyl which is optionally substituted one or several times with —OR, —C(O)NRR', heteroaryl, heterocyclyl, unsubstituted phenyl or phenyl substituted one or several times with alkoxy; and R$^4$ is heterocyclyl.

Such compounds, for example, may be selected from the group consisting of:

2-[8-Oxo-2-(tetrahydro-pyran-4-ylamino)-6-o-tolyl-8H-pyrido[3,4-d]pyrimidin-7-yl]-acetamide;

7-Methyl-2-(tetrahydro-pyran-4-ylamino)-6-o-tolyl-7H-pyrido[3,4-d]pyrimidin-8-one;

7-(1,5-Dimethyl-1H-pyrazol-3-ylmethyl)-2-(tetrahydro-pyran-4-ylamino)-6-o-tolyl-7H-pyrido[3,4-d]pyrimidin-8-one;

7-(3-Hydroxy-propyl)-2-(tetrahydro-pyran-4-ylamino)-6-o-tolyl-7H-pyrido[3,4-d]pyrimidin-8-one;

7-(3-Methoxy-benzyl)-2-(tetrahydro-pyran-4-ylamino)-6-o-tolyl-7H-pyrido[3,4-d]pyrimidin-8-one;

3-[8-Oxo-2-(tetrahydro-pyran-4-ylamino)-6-o-tolyl-8H-pyrido[3,4-d]pyrimidin-7-yl]-propionamide;

2-[6-(2-Chloro-phenyl)-8-oxo-2-(tetrahydro-pyran-4-ylamino)-8H-pyrido[3,4-d]pyrimidin-7-yl]-acetamide;

6-(2-Chloro-phenyl)-7-(1,5-dimethyl-1H-pyrazol-3-ylmethyl)-2-(tetrahydro-pyran-4-ylamino)-7H-pyrido[3,4-d]pyrimidin-8-one;

6-(2-Chloro-phenyl)-7-(3-hydroxy-propyl)-2-(tetrahydro-pyran-4-ylamino)-7H-pyrido[3,4-d]pyrimidin-8-one;

6-(2-Chloro-phenyl)-7-(3-methoxy-benzyl)-2-(tetrahydro-pyran-4-ylamino)-7H-pyrido[3,4-d]pyrimidin-8-one; and 6-(2-Chloro-phenyl)-7-(tetrahydro-furan-2-ylmethyl)-2-(tetrahydro-pyran-4-ylamino)-7H-pyrido[3,4-d]pyrimidin-8-one.

Another embodiment of the invention are the compounds of formula I, wherein

R$^1$ is halogen or alkyl;

R$^2$ is hydrogen;

R$^3$ is alkyl; and

R$^4$ is a) alkyl wherein the alkyl is optionally substituted one or several times with —OR or —NRR';

b) phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'; or c) heterocyclyl.

Another embodiment of the invention are the compounds of formula I, wherein

R$^3$ is alkyl which is substituted once with —OH.

Another embodiment of the invention are the compounds of formula I, wherein

R$^1$ is halogen or alkyl;

R$^2$ is hydrogen;

R$^3$ is alkyl which is substituted once with —OH; and

R$^4$ is a) alkyl wherein the alkyl is optionally substituted one or several times with —OR or —NRR';

b) phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'; or c) heterocyclyl.

Another embodiment of the invention are the compounds of formula I, wherein
$R^3$ is alkyl which is substituted once with —C(O)NRR'; and
R and R' are hydrogen.

Another embodiment of the invention are the compounds of formula I, wherein
$R^1$ is halogen or alkyl;
$R^2$ is hydrogen;
$R^3$ is alkyl which is substituted once with —C(O)NRR';
$R^4$ is a) alkyl wherein the alkyl is optionally substituted one or several times with —OR or —NRR';
b) phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'; or
c) heterocyclyl; and
R and R' are hydrogen Another embodiment of the invention are the compounds of formula I, wherein
$R^3$ is alkyl which is substituted once with heteroaryl.

Another embodiment of the invention are the compounds of formula I, wherein
$R^1$ is halogen or alkyl;
$R^2$ is hydrogen;
$R^3$ is alkyl which is substituted once with heteroaryl; and
$R^4$ is a) alkyl wherein the alkyl is optionally substituted one or several times with —OR or —NRR';
b) phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'; or
c) heterocyclyl.

Another embodiment of the invention are the compounds of formula I, wherein
$R^3$ is alkyl which is substituted once with heterocyclyl.

Another embodiment of the invention are the compounds of formula I, wherein
$R^1$ is halogen or alkyl;
$R^2$ is hydrogen;
$R^3$ is alkyl which is substituted once with heterocyclyl; and
$R^4$ is a) alkyl wherein the alkyl is optionally substituted one or several times with —OR or —NRR';
b) phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'; or
c) heterocyclyl.

Another embodiment of the invention are the compounds of formula I, wherein
$R^3$ is alkyl which is substituted once with phenyl substituted one or several times with alkoxy.

Another embodiment of the invention are the compounds of formula I, wherein
$R^1$ is halogen or alkyl;
$R^2$ is hydrogen;
$R^3$ is alkyl which is substituted once with phenyl substituted one or several times with alkoxy; and
$R^4$ is a) alkyl wherein the alkyl is optionally substituted one or several times with —OR or —NRR';
b) phenyl wherein the phenyl is optionally substituted one or several times with alkyl, alkoxy, heterocyclyl, —S(O)-alkyl or —S(O)$_2$NR-alkyl, and wherein all alkyl and alkoxy groups are optionally substituted one or several times with —OR or —NRR'; or
c) heterocyclyl.

Another embodiment of the invention is a process for the manufacture of the compounds of formula I, comprising the steps of
(a) reacting a compound of formula VIII

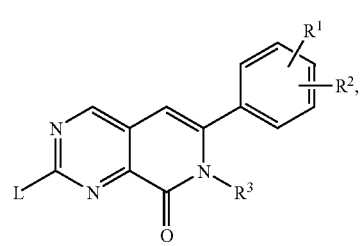

formula VIII wherein $R^1$, $R^2$ and $R^3$ have the significance given above for formula I and L is a leaving group selected from alkylsulfonyl or alkylsulfinyl, preferably L is alkylsulfonyl and more preferably methylsulfonyl, with a compound of formula VIIIa

$R^4$—NH$_2$        formula VIIIa, wherein $R^4$ has the significance given above for formula I, to give the respective compound of formula I,

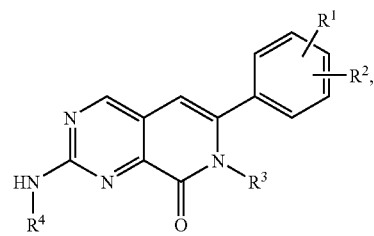

formula I wherein $R^1$, $R^2$, $R^3$ and $R^4$ have the significance given above for formula I, (b) said compound of formula I is isolated from the reaction mixture, and (c) if desired, converted into a pharmaceutically acceptable salt.

The derivatives of the general formula I or a pharmaceutically acceptable salt thereof, may be prepared by any process known to be applicable for the preparation of chemically-related compounds by the one skilled in the art. Such processes, when used to prepare the derivatives of formula I, or a pharmaceutically-acceptable salt thereof, are provided as a further feature of the invention and are illustrated by the following representative examples of scheme 1, in which, unless otherwise stated $R^1$, $R^2$, $R^3$ and $R^4$ have the significance given herein before for formula I. Necessary starting materials may be obtained by standard procedures of organic chemistry. The preparation of such starting materials is described within the accompanying examples. Alternatively necessary starting materials are obtainable by analogous procedures to those illustrated which are within the ordinary skill of an organic chemist.

Scheme 1

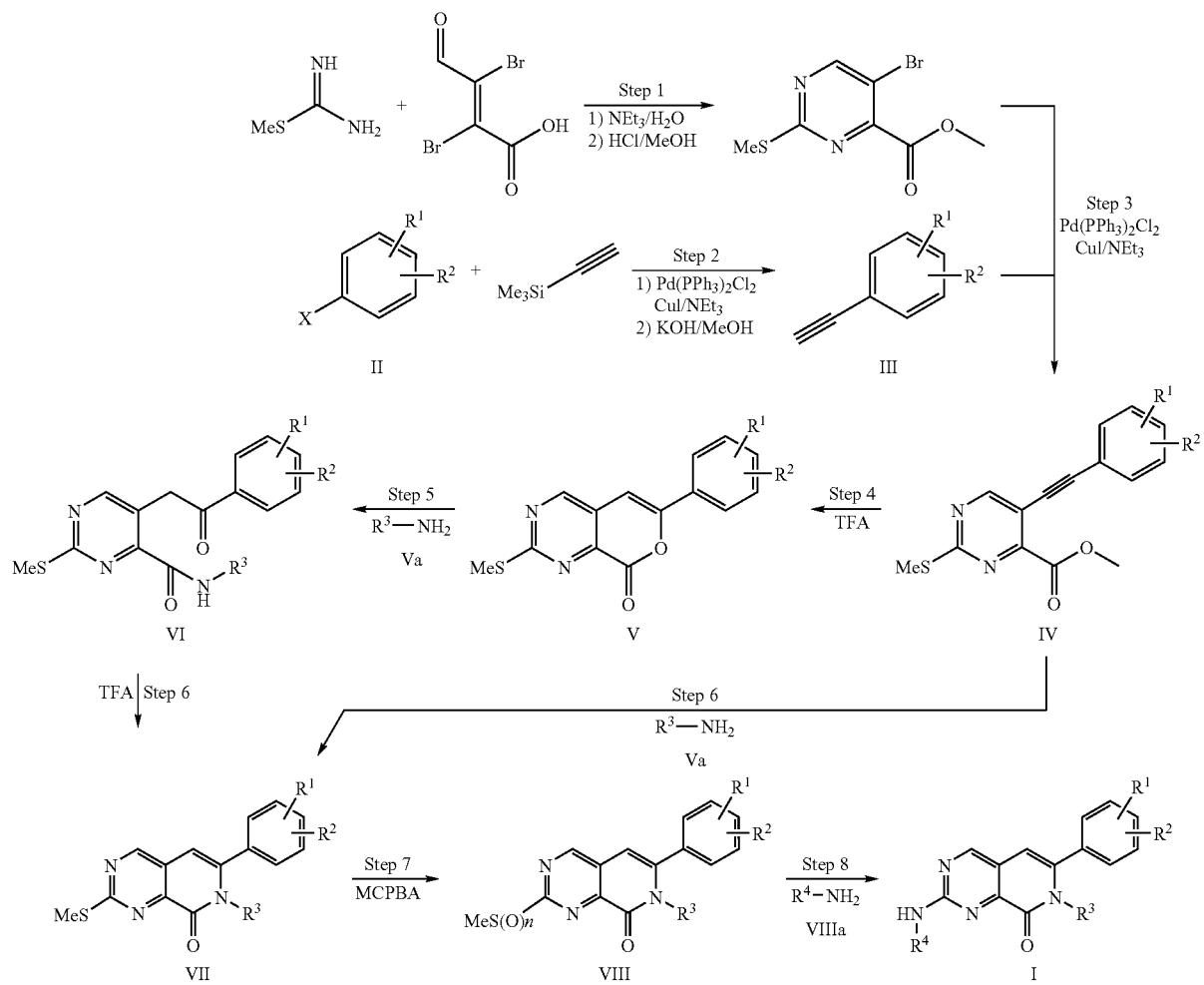

In scheme 1, $R^1$, $R^2$, $R^3$ and $R^4$ have the significance as given above for formula I, X is bromine or iodine and n is 1 or 2.

Step 1

5-bromo-2-methylsulfanyl-pyrimidine-4-carboxylic acid methyl ester is a known compound. The free carboxylic acid and can be prepared from mucobromic acid and S-methyl-isothiourea under basic conditions. It can further be converted to the methyl ester by standard procedures, e.g by condensation with methanol in the presence of anhydrous hydrochloric acid.

Step 2

Substituted phenylacetylenes of formula III are well known in the art and can be prepared from corresponding bromo- or iodoarenes of formula II and a protected ethyne by the so called Sonogashira reaction. This coupling reaction is performed with a copper catalyst like CuI or CuCl, and a palladium catalyst like $PdCl_2(PPh_3)_2$ or $PdCl_2(PhCN)_2$/ $PtBu_3$, and a base like di-isopropyl amine, diethyl amine or triethyl amine, which can also serve as the solvent, or in an inert solvent like tetrahydrofuran (THF), dioxane, N,N-dimethylformamide (DMF) or acetonitrile. The reaction proceeds at room temperature or higher, up to 160° C. A suitable protecting group on the ethyne is the trimethylsily group which can subsequently be cleaved off by treatment with a fluoride containing reagent like tetrabutyl ammonium fluoride in an inert aprotic solvent like tetrahydrofuran, or by a strong base like potassium hydroxide in alcohol solvents like methanol. This deprotection reaction is preferably done at moderate to low temperatures in the range from −30° C. to 50° C.

Step 3

The coupling of the phenylacetylenes of formula III to the 5-bromo-2-methylsulfanyl-pyrimidine-4-carboxylic acid methyl ester can be achieved under conditions of the so called Sonogashiro reaction as described for step 2.

Alternatively, the ethynyl-arene may first be converted into a more reactive alkynyl-Zn or -Sn derivative by procedures known in the art: the ethynyl-arene is deprotonated with a strong base like butyl lithium to form an alkynyl-Li intermediate which is reacted with $ZnCl_2$ or $Bu_3SnCl$ to yield the desired zinc or tin intermediate. These may subsequently be coupled to the 5-bromo-2-methylsulfanyl-pyrimidine-4-carboxylic acid methyl ester under standard cross coupling conditions, for instance by catalysis by a palladium phosphine complex like $Pd(PPh_3)_4$ or $PdCl_2(PPh_3)_2$ or $Pd_2(dba)_3$/$PtBu_3$ in solvents like dimethyl acetamide, THF, or toluene.

Step 4

Cyclisation of the ethynylpyrimidine derivatives of formula IV to pyranone derivatives of formula V can be achieved under acidic conditions, optionally in the presence of water.

This may be carried out a solvent like tetrahydrofuran, dioxane, N-methylpyrrolidinone or sulfolane. Suitable acids for this reaction can be trifluoroacetic acid, hydrochloric acid, sulfuric acid, toluene sulfonic acid, methane sulfonic acid, or polyphosphoric acid. The reaction can optionally be catalysed by mercury salts like HgO. Alternatively, a Lewis acid like $ZnBr_2$ is employed in an inert solvent like tetrahydrofuran.

Step 5

The pyranone derivatives of formula V are reacted with amines $R^3NH_2$ of formula Va to yield ring-opened pyrimidine carboxamides of formula VI. This can be achieved by heating the reaction partners neat in an excess of the amine, or in an inert solvent like dichloromethane, tetrahydrofuran (THF), ethanol, xylene, or N-methylpyrrolidinone (NMP) to a temperature in the range of 40° C. to 170° C. Optionally, an acid may be added to facilitate the reaction.

Step 6

The pyrimidine carboxamides of formula VI are again cyclized to pyrimidopyridones of formula VII by heating in the presence of an acid. In principle, the same conditions apply as described for step 4.

Step 6a

Alternatively, in certain cases the direct conversion of pyrimidine carboxylates of formula IV to the pyrimidopyridones of formula VII is possible by heating with the appropriate amine $R^3NH_2$ of formula Va neat or in an inert solvent like dichloromethane, tetrahydrofuran (THF), xylene, ethanol or N-methylpyrrolidinone (NMP). Optionally, an acid like trifluoroacetic acid or hydrochloric acid, or an transition metal catalyst like a palladium phosphin complex may be added to facilitate the reaction.

Step 7

The methylthio group of pyrimidopyridones VII is converted into a leaving group by oxidation to a methylsulfinyl or methylsulfonyl group. Suitable oxidants for this purpose are meta-chloroperbenzoic acid or 3-Phenyl-2-(toluene-4-sulfonyl)-oxaziridine in solvents like dichloromethane or THF, or Oxone or sodium periodate in methanol or THF/water mixtures. The oxidation reaction is performed at temperatures in the range of −20° C. to 60° C., and the resulting methylsulfinyl- or methylsulfonyl-pyrimidopyridones of formula VIII (n=1 or 2) may optionally be used directly without isolation in step 8.

Step 8

The methylsulfinyl or methylsulfonyl group of compounds of formula VIII is displaced by an amine $R^4NH_2$ of formula VIIIa to yield the final products of formula I by heating the reactants neat, or diluted with an inert solvent like N-methylpyrrolidionone, dimethylacetamide, sulfolane, dichloromethane, tetrahydrofuran (THF) or acetonitrile. An acid like trifluoroacetic acid or anhydrous hydrochloric acid may be added to facilitate the reaction. The reaction is carried out at elevated temperatures in the range from 60° C. to 180° C. Alternatively, the amines $R^4NH_2$ may be deprotonated by a strong base like lithium hexamethyldisilazide or lithium diisopropylamide and reacted with compounds of formula VIII at temperatures between −50° C. and room temperature in an inert solvent like diethyl ether or THF.

The compounds according to the present invention may exist in the form of their pharmaceutically acceptable salts. The term "pharmaceutically acceptable salt" refers to conventional acid-addition salts that retain the biological effectiveness and properties of the compounds of formula I and are formed from suitable non-toxic organic or inorganic bases or from organic or inorganic acids. Examples of base-addition salts include those derived from sodium, potassium, ammonium, quaternary ammonium hydroxides (such as for example, tetramethylammonium hydroxide), especially from sodium. Examples of acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. The chemical modification of a pharmaceutical compound (i.e. a drug) into a salt is a technique well known to pharmaceutical chemists to obtain improved physical and chemical stability, hygroscopicity, flowability and solubility of compounds. See e.g. Stahl, P. H., and Wermuth, G., (editors), Handbook of Pharmaceutical Salts, Verlag Helvetica Chimica Acta (VHCA), Zürich, (2002) or Bastin, R. J., et al., Organic Proc. Res. Dev. 4 (2000) 427-435.

The compounds of formula I can contain one or several chiral centers and can then be present in a racemic or in an optically active form. The racemates can be separated according to known methods into the enantiomers. For instance, diastereomeric salts which can be separated by crystallization are formed from the racemic mixtures by reaction with an optically active acid such as e.g. D- or L-camphorsulfonic acid. Alternatively separation of the enantiomers can also be achieved by using chromatography on chiral HPLC-phases which are commercially available.

Medicaments containing a compound of the present invention or a pharmaceutically acceptable salt thereof and a therapeutically inert carrier are an object of the present invention, as is a process for their production, which comprises bringing one or more compounds of the present invention and/or pharmaceutically acceptable salts and, if desired, one or more other therapeutically valuable substances into a galenical administration form together with one or more therapeutically inert carriers.

An embodiment of the invention is a pharmaceutical composition, containing one or more compounds according to formula I, together with pharmaceutically acceptable excipients.

Another embodiment of the invention is a pharmaceutical composition, containing one or more compounds according to formula I, for the inhibition of tumor growth.

Another embodiment of the invention is a pharmaceutical composition, containing one or more compounds according to formula I, for the treatment of cancer.

Another embodiment of the invention is a medicament containing one or more compounds of formula I as active ingredients together with pharmaceutically acceptable adjuvants for the treatment of colorectal, breast, lung, prostate, pancreatic, gastric, bladder, ovarian, melanoma, neuroblastoma, cervical, kidney or renal cancers, leukemias or lymphomas.

Another embodiment of the invention is the use of a compound according to formula I, for the manufacture of corresponding medicaments for the inhibition of tumor growth.

Another embodiment of the invention is the use of a compound according to formula I, for the manufacture of corresponding medicaments for the treatment of cancer.

Another embodiment of the invention is the use of the compounds of formula I as anti-proliferating agents.

Another embodiment of the invention is the use of one or more compounds of formula I for the treatment of cancer.

Pharmacological Activity

The compounds of formula I and their pharmaceutically acceptable salts possess valuable pharmacological properties. It has been found that said compounds show show activity as Src family tyrosine kinase inhibitors Consequently the compounds of the present invention are useful in the therapy and/or prevention of proliferative diseases such as cancer. The activity of the present compounds as is demonstrated e.g. by the following biological assay:

Src-Inhibitor-Assay Parameters:
Reaction Mixture:
ATP 5 µM
Peptide (Ro+Ja133-Ro): 10 µM
   Ja133-Ro 196 nM
   Ro 9.8 µM
PT66 230 ng/ml
Assay buffer: 4 mM $MgCl_2$
   2 mM TCEP
   50 mM HEPES
   0.1% Tween 20
   pH 7.3
Enzyme: 2.5 U/ml
Inhibitor: max. 25 µM
   min. 0.42 nM
Material:
Eu-labelled phosphotyrosine antibody: —for Lck Cisbio Mab PT66-K,
   for Src EG&G Wallac PT66 Eu-W1024 (all commercially available).
Peptides: Ro: $NH_2$-A-E-E-E-I-Y-G-E-F-E-A-K-K-K-K-$CONH_2$, and
   Ja133-Ro: Ja133-G-Aminocaprylic acid-A-E-E-E-I-Y-G-E-F-E-A-K-K-K-K-$CONH_2$, wherein Ja133 is Light-Cycler-Red 640-N-hydroxy succinimide ester;
   whereby both peptides were synthesized by an optimized solid phase peptide synthesis protocol (Merrifield, Fed. Proc. Fed. Amer. Soc. Exp. Biol. 21 (1962) 412) on a Zinsser SMP350 peptide synthesizer. Shortly, the peptide was assembled on 160 mg (22.8 µmol scale) of a Rink-Linker modified polystyrene solid phase by repeatedly conjugating an twenty fold excess of amino acids each protected by temporary piperidine labile Fmoc- and permanent acid labile tert-Bu-, BOC- and O-tert-Bu-groups depending on the side chain function. The substrate sequence AEEEIYGEFEAKKKK was N-terminal additionally mounted with the spacer amino acids Aminocaprylic acid and Glycin. After cleavage of the N-terminal temporary protecting group the still attached and protected peptide was labeled with a 1.5 fold amount of LightCycler-Red 640-N-hydroxy succinimide ester (purchased from Roche Diagnostics GmbH) and triethylamine. After 3 hrs. the resin was washed with Dimethylformamide and Isopropanol until the eluates of the blue resin got colourless. The fully protected and labeled peptide was removed from the solid phase and released from the permanent protecting groups by treatment with a mixture of 80% trifluoroacetic acid, 10% Ethanedithiol, 5% Thioanisol and 5% Water. The substrate was finally isolated by a preparative reverse phase HPLC purification. The purification yielded 12.2 mg RP-HPLC single peak pure blue material (lyophilisate). The identity was proven by MALDI mass spectroscopy [2720.0].
Enzymes: Upstate Lck ($p56^{lck}$, active), Upstate Src ($p60^{c-src}$, partially purified) were purchased from UBI, Upstate Biotech, Inc.

Time-resolved Fluorescence Assay: Reader: Perkin Elmer, Wallac Viktor 1420-040 multilabel counter; Liquid handling system: Beckman Coulter, Biomek 2000.

ATP, Tween™ 20, 4-(2-hydroxyethyl)-1-piperazineethanesulfonic acid (HEPES) were purchased from Roche Molecular Biochemicals, $MgCl_2$ and $MnCl_2$ were purchased from Merck Eurolab, Tris(2-carboxyethyl)phosphine hydrochloride (TCEP) was purchased from Pierce, 384 Well low volume fluorescence plates was purchased from Falcon.

Assay Description:
At first the enzyme is pre-incubated for 15 min. at 15° C. in aqueous solution with corresponding amounts of inhibitors according to this invention. Then the phosphorylation reaction is started by adding a reaction mixture, containing ATP, Peptide and PT66, and subsequent shaking. The proceeding of this reaction is immediately monitored using time resolved fluorescence spectroscopy in a suitable well plate reader.

The $IC_{50}$-values can be obtained from the reaction rates by using a non-linear curve fit (XLfit software (ID Business Solution Ltd., Guilford, Surrey, UK)). The results are shown in Table 1.

TABLE 1

| Example-No. | IC50 src [µM] |
| --- | --- |
| 1 | 0.0029 |
| 12 | 0.687 |
| 3, 5, 6, 7, 8, 10, 20, 21, 23, 30, 31, 33, 37 | 0.001-0.500 |
| 4 | 0.500-1.500 |

$IC_{50}$ Determination for Inhibitors of Abl Kinase

Abl assay was done using fusion protein corresponding to mouse Abl (27-end) fluorescein labeled peptide substrate (with a sequence of EAIYAAPFAKKK) and quantified by Molecular Devices' IMAP fluorescence polarization technology. Compounds were tested in serially diluted concentrations in 384 well plates. Kinase reaction was performed in KAB Buffer (10 mM HEPES, pH 7, 50 mM NaCl, 5 mM $MgCl_2$, 1 mM DTT, 0.1 mM $NaVO_4$, 0.02% BSA), in the presence of 22.8 uM ATP, incubated at 37° C. for 60 minutes. Reaction was stopped by IMAP bead mix (at 1:400 diluted). After incubation at room temperature for 3 hours, the reaction product was analyzed on LJL Acquest (excitation 485 nM and Emission 530 nM).

FP reading (in mP) was used to calculate reaction rate. The assay was semi-automated by Tomtec Quadra workstation. The results are shown in Table 2.

TABLE 2

| Example No. | IC50 Abl kinase inhibition [µM] |
| --- | --- |
| 5 | 0.077 |
| 8 | 0.214 |
| 1, 3, 6, 7, 10, 20, 21, 22, 23, 30, 31, 33, 37 | 0.001-0.500 |
| 4, 12 | 0.500-15.00 |

$IC_{50}$ Determination for Inhibitors of PDGFR Kinase
Assay Principle

PDGFR assay was carried out with human recombinant PDGFR beta, fluorescein labeled peptide substrate (with a peptide sequence of ALTSNQEYLDLSMPL) and test compounds (in serial dilution) using 384-well plates. Kinase reaction was performed in MOPS buffer (20 mM MOPS pH 7.1, 5 mM Sodium Acetate, 6.25 mM $MgCl_2$, 0.5 mM EDTA, 1 mM DTT, 0.04 mM NaVO$_4$, 0.02% BSA), in the presence of 48 uM ATP, incubated at room temperature for 60 minutes. Reaction was stopped by IMAP Bead Binding System (Molecular Devices). After incubation at room temperature for 2 hours, the reaction product was analyzed on LJL Acquest.

FP reading (in mP) was used to calculate reaction rate. The assay was semi-automated by Tomtec Quadra workstation. The results are shown in Table 3.

TABLE 3

| Example No. | IC50 PDGFR kinase inhibition [µM] |
|---|---|
| 3 | 0.094 |
| 10 | 0.417 |
| 1, 3, 6, 7 | 0.001-0.500 |
| 20, 30 | 0.500-15.00 |

Antiproliferative Activity

The activity of the present compounds as antiproliferative agents can be demonstrated by the following biological assay: CellTiter-Glo™ Assay in HCT 116 Cells The CellTiter-Glo™ Luminescent Cell Viability Assay (Promega) is a homogeneous method of determining the number of viable cells in culture based on quantitation of the ATP present, which signals the presence of metabolically active cells.

HCT 116 cells (human colon carcinoma, ATCC-No. CCl-247) is cultivated in RPMI 1640 medium with GlutaMAX™ (Invitrogen, Cat-No. 61870-010), 5% Fetal Calf Serum (FCS, Sigma Cat-No. F4135 (FBS)); 100 Units/ml penicillin/100 µg/ml streptomycin (=Pen/Strep from Invitrogen Cat. No. 15140). For the assay the cells are seeded in 384 well plates, 1000 cells per well, in the same medium. The next day the test compounds are added in various concentrations ranging from 30 µM to 0.0015 µM (10 concentrations, 1:3 diluted). After 5 days the CellTiter-Glo™ assay is done according to the instructions of the manufacturer (CellTiter-Glo™ Luminescent Cell Viability Assay, from Promega). In brief: the cell-plate is equilibrated to room temperature for approximately 30 minutes and than the CellTiter-Glo™ reagent is added. The contents are carefully mixed for 15 minutes to induce cell lysis. After 45 minutes the luminescent signal is measured in Victor 2, (scanning multiwell spectrophotometer, Wallac).

Details:
1st. day:
  Medium: RPMI 1640 with GlutaMAX™ I (Invitrogen, Cat-Nr. 61870), 5% FCS (Sigma Cat.-No. F4135), Pen/Strep (Invitrogen, Cat No. 15140).
  HCT116 (ATCC-No. CCl-247): 1000 cells in 60 µl per well of 384 well plate (Greiner 781098, µClear-plate white)
  After seeding incubate plates 24 h at 37° C., 5% CO$_2$
2nd. Day: Induction (Treatment with Compounds, 10 Concentrations):
  In order to achieve a final concentration of 30 µM as highest concentration 3.5 µl of 10 mM compound stock solution is added directly to 163 µl media. Then step e) of the dilution procedure described below, is followed.
  In order to achieve the second highest to the lowest concentrations, a serial dilution with dilution steps of 1:3 is followed according to the procedure (a-e) as described here below:
  a) for the second highest concentration add 10 µl of 10 mM stock solution of compound to 20 µl dimethylsulfoxide (DMSO)
  b) dilute 8×1:3 (always 10 µl to 20 µl DMSO) in this DMSO dilution row (results in 9 wells with concentrations from 3333.3 µM to 0.51 µM)
  c) dilute each concentration 1:47.6 (3.5 µl compound dilution to 163 µl media)
  d) add 10 µl of every concentration to 60 µl media in the cell plate resulting in final concentration of DMSO: 0.3% in every well and resulting in 10 final concentration of compounds ranging from 30 µM to 0.0015 µM.
  Each compound is tested in triplicate.
  Incubate 120 h (5 days) at 37° C., 5% CO$_2$
Analysis:
  Add 30 µl CellTiter-Glo™ Reagent (prepared from CellTiter-Glo™ Buffer and CellTiter-Glo™ Substrate (lyophilized) purchased from Promega) per well,
  shake 15 minutes at room temperature
  incubate further 45 minutes at room temperature without shaking
Measurement:
  Victor 2 scanning multiwell spectrophotometer (Wallac), Luminescence mode (0.5 sec/read, 477 nm)
  Determine IC50 using a non-linear curve fit (XLfit software (ID Business Solution Ltd., Guilford, Surrey, UK))

The compounds according to this invention and their pharmaceutically acceptable salts can be used as medicaments, e.g. in the form of pharmaceutical compositions. The pharmaceutical compositions can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The above-mentioned pharmaceutical compositions can be obtained by processing the compounds according to this invention with pharmaceutically inert, inorganic or organic carriers. Lactose, corn starch or derivatives thereof, talc, stearic acids or it's salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

A pharmaceutical compositions comprise e.g. the following:

a) Tablet Formulation (Wet Granulation):

| Item | Ingredients | mg/tablet | | | |
|---|---|---|---|---|---|
| 1. | Compound of formula (I) | 5 | 25 | 100 | 500 |
| 2. | Lactose Anhydrous DTG | 125 | 105 | 30 | 150 |

-continued

| Item | Ingredients | mg/tablet | | | |
|---|---|---|---|---|---|
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure:

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

b) Capsule Formulation:

| Item | Ingredients | mg/capsule | | | |
|---|---|---|---|---|---|
| 1. | Compound of formula (I) | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure:

1. Mix items 1, 2 and 3 in a suitable mixer for 30 minutes.
2. Add items 4 and 5 and mix for 3 minutes.
3. Fill into a suitable capsule.

The following examples are provided to aid the understanding of the present invention, the true scope of which is set forth in the appended claims. It is understood that modifications can be made in the procedures set forth without departing from the spirit of the invention.

EXPERIMENTAL PROCEDURES

Experimental Methods $^1$H-NMR spectra were recorded using a Bruker 250 Avance spectrometer. Chemical shifts were reported in parts per million (ppm) on the δ scale relative to trimethylsilane internal standard. Identification and purity were determined by Analytical LC-MS performed on a HP1100 system using a Phenomenex Gemini C18 column (5 μm, 30 mm×2.0 mm), mobile phase 5-95% acetonitrile/water (containing 0.05% ammonia) over 4.5 min, hold for 1.5 min, flow rate, 1 ml/min, diode array detection at 210-220 nm. The mass spectrometer was a Micromass Platform LC operating in switchable positive and negative ion electrospray modes. Analytical GC was carried out on an Agilent 6890N GC system using a Z5-5 column (15 m, 0.32 mm×0.25 mm), 50° C. hold for 2.5 min, 50° C.-275° C. over 10 min, 1 ml/min, injector temperature 300° C., flame ionisation detection at 300° C.

Microwave reactions were carried out in heavy-walled glass Smith process vials with aluminium crimp caps fitted with a silicone septum. Microwave heating was performed in a Personal Chemistry Creator EXP system to the specified temperature and for the specified duration. All reactions were carried out under an atmosphere of nitrogen.

Synthesis of Key Intermediates

Example A 5-bromo-2-methylsulfanylpyrimidine-4-carboxylic acid methyl ester

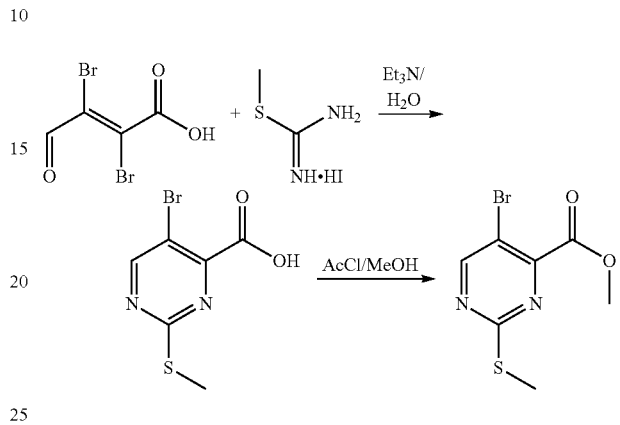

Triethylamine (161.5 ml, 1.16 mol) was added dropwise over 25 min to a stirred suspension of 5-methylisothiourea hydroiodide (85.0 g, 0.39 mol) and mucobromic acid (100.0 g, 0.39 mol) in water (500 ml). During this time an exotherm was observed (20° C. to 50° C.). The mixture was stirred for 18 h at ambient temperature, then it was acidified at 0-5° C. to pH 2 using 10% hydrochloric acid. The resulting precipitate was collected by filtration and dried in vacuo to give 5-bromo-2-methylsulfanyl-pyrimidine-4-carboxylic acid (71.4 g) as a brown solid, which was used without further purification.

Acetyl chloride (6.26 ml, 0.088 mol) was added dropwise at 0-5° C. to methanol (100 ml). The mixture was stirred at 0-5° C. for 5 min. 5-Bromo-2-methylsulfanylpyrimidine-4-carboxylic acid (20 g, 0.08 mol) was added in portions at 0-5° C. then the mixture was heated under reflux for 1 h, during which time the slurry dissolved, then it was cooled to ambient temperature and poured into saturated aqueous sodium hydrogencarbonate solution (100 ml). The product was extracted into dichloromethane (3×100 ml), the extracts were washed with water (100 ml), dried (MgSO$_4$) and evaporated in vacuo. The residual solid was crystallised from hexane to give 5-bromo-2-methylsulfanylpyrimidine-4-carboxylic acid methyl ester (12.27 g) as an off white crystalline solid, m.pt. 67-70° C.; 250 MHz $^1$H-NMR (CDCl$_3$) δ (ppm): 2.6 (s, 3H) (—SCH$_3$), 4.05 (s, 3H) (—OCH$_3$), 8.7 (s, 1H) (ArH); m/z (M+H)$^+$. 249; HPLC purity 96%; HPLC retention time 1.58 min.

Substituted phenylacetylenes of formula II were literature known or prepared according to the following examples B1 and B2:

Example B1

1-ethynyl-2-methylbenzene

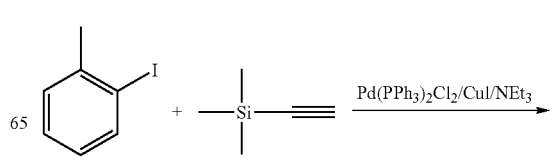

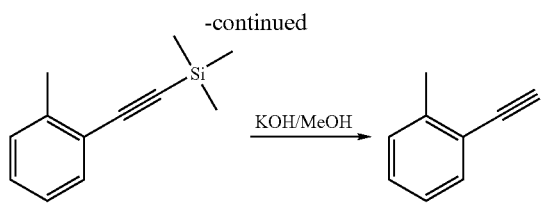

2-Iodotoluene (81.5 ml, 0.64 mol) and trimethylsilylacetylene (99 ml, 0.71 mol) were dissolved in triethylamine (250 ml). Triphenylphosphine (0.427 g, 1.6 mmol), copper (I) iodide (0.3 g, 1.6 mmol) and bistriphenyphosphinepalladium (II) dichloride (0.53 g, 0.71 mmol) were added and the mixture was heated under reflux for 18 h. The mixture was cooled to ambient temperature and carefully added to 10% hydrochloric acid (480 ml) and the product was extracted into hexane (3×200 ml). The extracts were washed with 10% hydrochloric acid (200 ml) and water (2×200 ml) then dried (MgSO$_4$) and evaporated in vacuo to give trimethyl-(2-methylphenyl)ethynylsilane (114.06 g) as a yellow oil, which was used without further purification.

Potassium hydroxide (10 g, 1.8 mol) added in 4 portions to a stirred solution of trimethyl-(2-methylphenyl)ethynylsilane (114.0 g, 0.61 mol) in methanol (400 ml) at 0° C. The mixture was stirred at 0° C. until the reaction was complete (by tlc 1:1 ethyl acetate:hexane). The mixture was neutralised by the addition of 10% hydrochloric acid and the product was extracted into dichloromethane (2×150 ml). The combined extracts were dried (MgSO$_4$) and evaporated in vacuo. The residual oil was purified by short path distillation (Kugelrohr) to give 1-ethynyl-2-methylbenzene (52.03 g) as a clear oil. B.pt. 45° C./12 mBar. 250 MHz $^1$H-NMR (CDCl$_3$) δ (ppm): 2.35 (s, 3H) (ArCH$_3$), 3.2 (s, 1H)(CH), 7.0-7.2 (m, 3H) (3×ArH), 7.4 (m, 1H) (ArH); GC purity 98%, GC retention time 7.94 min.

Example B2

1-chloro-2-ethynylbenzene

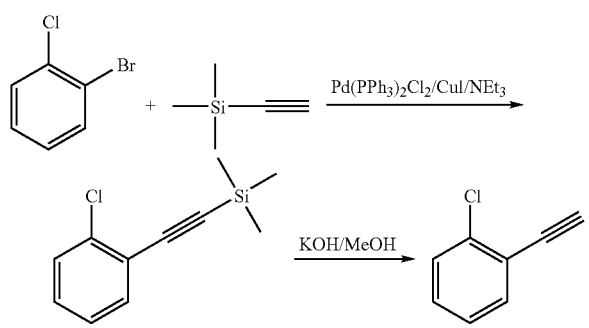

2-Bromochlorobenzene (54.1 ml, 0.46 mol) and trimethylsilylacetylene (72 ml, 0.51 mol) were dissolved in triethylamine (250 ml). Triphenylphosphine (0.4 g, 1.5 mmol), copper (I) iodide (0.3 g, 1.6 mmol) and bistriphenyphosphinepalladium (II) dichloride (0.5 g, 0.67 mmol) were added and the mixture was heated under reflux for 18 h. The reaction mixture was cooled to ambient temperature and carefully added to 10% hydrochloric acid (480 ml). The product was extracted into hexane (3×200 ml), the extracts were washed with 10% hydrochloric acid (200 ml) and water (2×200 ml) then dried (MgSO$_4$) and evaporated in vacuo to give (2-chlorophenylethynyl)-trimethylsilane (95.4 g) as an orange oil, which was used without further purification.

Potassium hydroxide (77.5 g, 1.38 mol) was added in 4 portions to a stirred solution of (2-chlorophenylethynyl)-trimethylsilane (95.0 g, 0.46 mol) in methanol (250 ml) at 0° C. The mixture was stirred at 0° C. until the reaction was complete (by tlc 1:1 ethyl acetate:hexane). The mixture was neutralised by the addition of 10% hydrochloric acid and the product was extracted into dichloromethane (2×150 ml). The combined extracts were dried (MgSO$_4$) and evaporated in vacuo. The residual oil was purified by short path distillation (Kugelrohr) to give 1-chloro-2-ethynylbenzene (41.23 g) as a clear oil. B.pt. 38° C./10 mBar. 250 MHz $^1$H-NMR (CDCl$_3$) δ (ppm): 3.25 (s, 1H)(CH), 7.1-7.5 (m, 4H) (ArH); GC purity 89%, GC retention time 2.67 min.

Example C1

2-methylsulfanyl-6-(2-methylphenyl-pyrano[3,4-d]pyrimidin-8-one

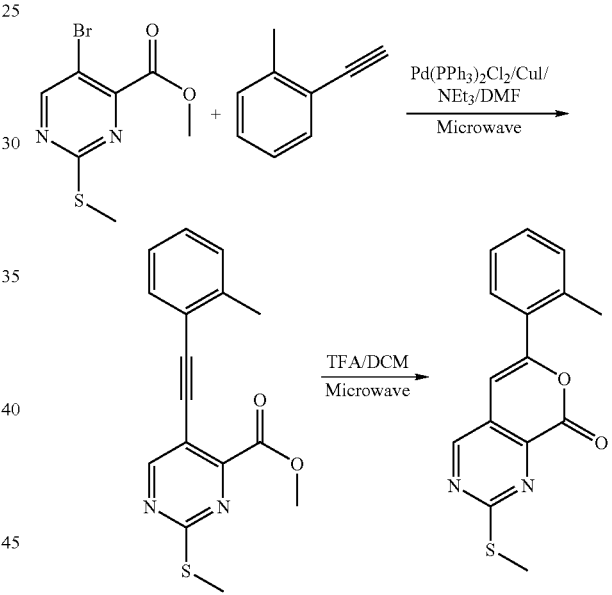

A mixture of 1-ethynyl-2-methylbenzene (0.53 g, 4.6 mmol), 5-bromo-2-methylsulfanylpyrimidine-4-carboxylic acid methyl ester (11.0 g, 3.8 mmol), triethylamine (2.5 ml), triphenylphosphine (0.125 g, 0.48 mmol), copper (I) iodide (0.025 g, 0.13 mmol), bistriphenyphosphinepalladium (II) dichloride (0.10 g, 0.14 mmol) and dimethylformamide (1 ml) was stirred in a heavy-walled Smith process vial and irradiated with microwaves to maintain 100° C. for 20 min. The cooled mixture was diluted with dichloromethane (20 ml) and washed with 5% hydrochloric acid (20 ml), water (20 ml), saturated aqueous sodium hydrogencarbonate solution (20 ml) and water (20 ml) then dried (MgSO$_4$) and evaporated in vacuo. The residual oil was purified by flash column chromatography over silica using a 1:4 mixture of hexane and dichloromethane as eluant. Appropriate fractions were combined and the solvents removed in vacuo to give 2-methyl-sulfanyl-5-(2-methylphenyl)ethynylpyrimidine-4-carboxylic acid methyl ester (0.9 g) as an orange oil. 250 MHz $^1$H-NMR (CDCl$_3$) δ (ppm): 2.45 (s, 3H) (ArCH$_3$), 2.55 (s, 3H) (—SCH$_3$), 3.95 (s, 3H)(CO$_2$CH$_3$), 7.05-7.25 (m, 3H) (3×ArH), 7.45 (m, 1H) (ArH), 8.7 (s, 1H) (ArH); m/z (M+H)$^+$. 299, HPLC purity 96%, HPLC retention time 4.15 min.

A mixture of 2-methylsulfanyl-5-(2-methylphenyl)ethynylpyrimidine-4-carboxylic acid methyl ester (5.0 g, 16.8 mmol) (prepared in a manner similar to that described above), 50% (v/v) trifluoroacetic acid in dichloromethane (15 ml) and water (1 ml) was stirred in a heavy-walled Smith process vial and irradiated to 120° C. for 45 min. The mixture was evaporated in vacuo to dryness and the residual oil was purified by flash column chromatography over silica using a 3:7 mixture of hexane and dichloromethane as eluant. Appropriate fractions were combined and the solvents removed in vacuo to give 2-methylsulfanyl-6-(2-methylphenyl-pyrano[3,4-d]pyrimidin-8-one (3.75 g) as an orange oil. 250 MHz $^1$H-NMR (CDCl$_3$) δ (ppm): 2.45 (s, 3H) (ArCH$_3$), 2.65 (s, 3H) (—SCH$_3$), 6.45 (s, 1H) (=CHAr), 7.15-7.45 (m, 4H) (4×ArH), 8.85 (s, 1H) (ArH); m/z (M+H)$^+$. 285, HPLC purity 98%, HPLC retention time 3.64 min.

Example C2

6-(2-chlorophenyl)-2-methylsulfanylpyrano[3,4-d]pyrimidin-8-one

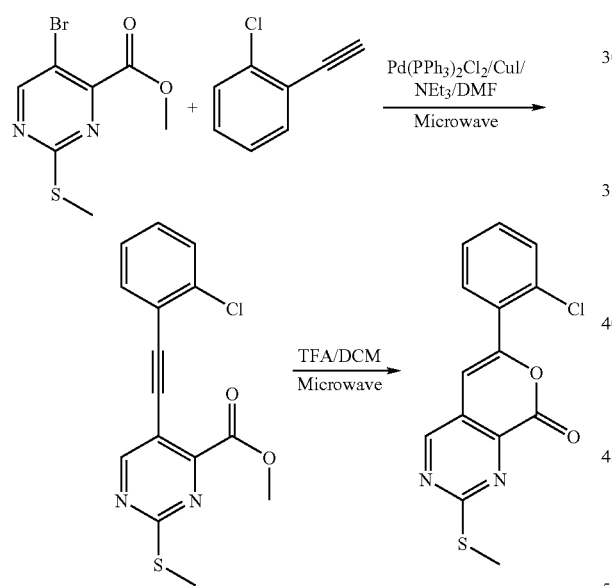

A mixture of 1-chloro-2-ethynylbenzene (0.63 g, 4.6 mmol), 5-bromo-2-methylsulfanylpyrimidine-4-carboxylic acid methyl ester (1.0 g, 3.8 mmol), triethylamine (2.5 ml), triphenylphosphine (0.125 g, 0.48 mmol), copper (I) iodide (0.025 g, 0.13 mmol), bistriphenyphosphinepalladium (II) dichloride (0.10 g, 0.14 mmol) and dimethylformamide (1 ml) was stirred in a heavy-walled Smith process vial and irradiated with microwaves to maintain 100° C. for 20 min. The mixture was diluted with dichloromethane (20 ml) and washed with 5% hydrochloric acid (20 ml), water (20 ml), saturated aqueous sodium hydrogencarbonate solution (20 ml) and water (20 ml) then dried (MgSO$_4$) and evaporated in vacuo. The residual oil was purified by flash column chromatography over silica using a 1:4 mixture of hexane and dichloromethane as eluant. Appropriate fractions were combined and the solvents removed in vacuo to give 5-(2-chlorophenylethynyl)-2-methylsulfanylpyrimidine-4-carboxylic acid methyl ester (0.9 g) as a yellow oil. 250 MHz $^1$H-NMR (CDCl$_3$) δ (ppm): 2.5 (s, 3H) (—SCH$_3$), 3.9 (s, 3H) (—CO$_2$CH$_3$), 7.1-7.5 (m, 4H) (ArH), 8.65 (s, 1H) (ArH); m/z (M+H)$^+$. 319, HPLC purity 91%, HPLC retention time 4.08 min.

A mixture of 5-(2-chloro-phenylethynyl)-2-methylsulfanyl-pyrimidine-4-carboxylic acid methyl ester (5.0 g, 9.4 mmol) (prepared in a manner similar to that described above), 50% (v/v) trifluoroacetic acid in dichloromethane (15 ml) and water (1 ml) was stirred in a heavy-walled Smith process vial and irradiated to 120° C. for 45 min. The mixture was evaporated in vacuo to dryness and the residual oil was purified by flash column chromatography over silica using a 3:7 mixture of hexane and dichloromethane as eluant. Appropriate fractions were combined and the solvents removed in vacuo to give 6-(2-chlorophenyl)-2-methylsulfanylpyrano[3,4-d]pyrimidin-8-one (3.15 g) as a pale yellow oil. 250 MHz $^1$H-nmr (CDCl$_3$) δ (ppm): 2.65 (s, 3H) (—SCH$_3$), 6.95 (s, 1H) (=CHAr), 7.25-7.4 (m, 3H) (ArH), 7.65 (m, 1H) (ArH), 8.85 (s, 1H) (ArH); m/z (M+H)$^+$. 305, HPLC purity 100%, HPLC retention time 3.66 min.

Example D

2-Methylsulfanyl-5-(2-oxo-2-o-tolyl-ethyl)-pyrimidine-4-carboxylic acid amides

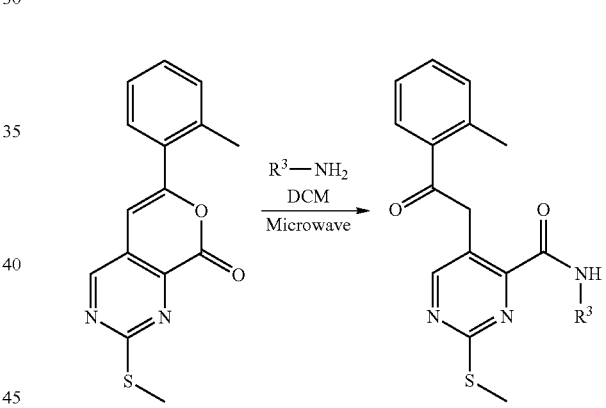

A mixture of 2-methylsulfanyl-6-(2-methylphenyl)-pyrano[3,4-d]pyrimidin-8-one (0.5 g, 1.8 mmol), the appropriate amine (3.6 mmol) and dichloromethane (3.5 ml) was stirred in a heavy-walled Smith process vial and irradiated to 120° C. for 15 min. The mixture was diluted with dichloromethane (10 ml), washed with water (2×10 ml) then dried (MgSO$_4$) and evaporated in vacuo to give the desired amide as dark oil in each case, which was used without further purification.

Compounds Synthesized:

| Example No | R$^3$ | m/z (MH$^+$) | Retention time (minutes) | Purity (%) |
|---|---|---|---|---|
| D1 | —Me | 316 | 3.46 | 100 |
| D2 | ⟍⟋OH | 346 | 3.22 | 100 |

-continued

| Example No | R³ | m/z (MH⁺) | Retention time (minutes) | Purity (%) |
|---|---|---|---|---|
| D3 | propanamide | 359 | 3.13 | 87 |
| D4 | 1,5-dimethyl-3-ethylpyrazole | 410 | 3.61 | 91 |
| D5 | propyl-imidazole | 396 | 3.37 | 95 |
| D6 | H | 302 | 3.26 | 100 |
| D7 | butanol | 360 | 3.29 | 100 |
| D8 | dimethylaminopropyl | 373 | 3.68 | 84 |
| D9 | butanamide | 373 | 3.14 | 90 |
| D10 | isobutyl | 344 | 3.85 | 98 |
| D11 | 3-methoxybenzyl | 422 | 4.02 | 91 |
| D12 | methylpyrazole | 368 | 3.49 | 97 |
| D13 | 4-methyl-N-Boc-piperidine | 485 | 4.18 | 94 |
| D14 | ethyl-tetrahydrofuran | 386 | 3.69 | 100 |

Example E 7-substituted-2-methylsulfanyl-6-o-tolyl-7H-pyrido[3,4-d]pyrimidin-8-ones

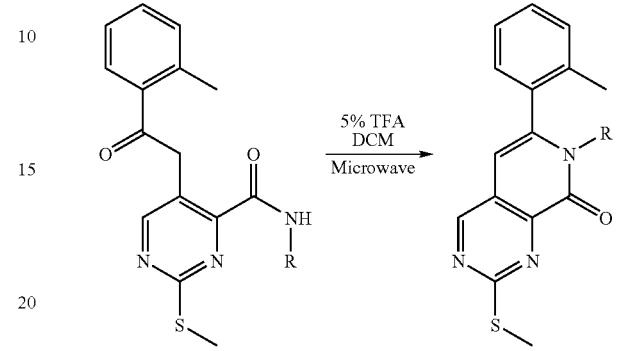

A mixture of the appropriate amide (1.8 mmol) (prepared in (D)) and 10% (v/v) trifluoroacetic acid in dichloromethane (4 ml) was stirred in a heavy walled Smith process vial and irradiated to 120° C. for 20 min. The mixture was poured into saturated aqueous sodium hydrogencarbonate solution (20 ml) and the product extracted into dichloromethane (2×20 ml). The combined extracts were dried (MgSO₄) and evaporated in vacuo to give the desired lactam, which was used without further purification.

Compounds Synthesized:

| Example No | R³ | m/z (MH⁺) | Retention time (minutes) | Purity (%) |
|---|---|---|---|---|
| E1 | —Me | 298 | 3.35 | 100 |
| E2 | propanol | 328 | 3.13 | 97 |
| E3 | propanamide | 341 | 2.1 | 86 |
| E4 | 1,5-dimethyl-3-ethylpyrazole | 392 | 2.97 | 76 |
| E5 | H | 284 | 2.4 | 100 |
| E6 | butanol | 342 | 3.26 | 84 |
| E7 | butanamide | 355 | 3.11 | 79 |
| E8 | isobutyl | 326 | 3.64 | 77 |

-continued

| Example No | R³ | m/z (MH⁺) | Retention time (minutes) | Purity (%) |
|---|---|---|---|---|
| E9 | 3-methoxybenzyl (CH₂-C₆H₄-OMe) | 404 | 3.79 | 89 |
| E10 | (tetrahydrofuran-2-yl)methyl | 368 | 3.59 | 75 |

Example F

2-Methanesulfonyl-7-substituted-6-o-tolyl-7H-pyrido[3,4-d]pyrimidin-8-ones

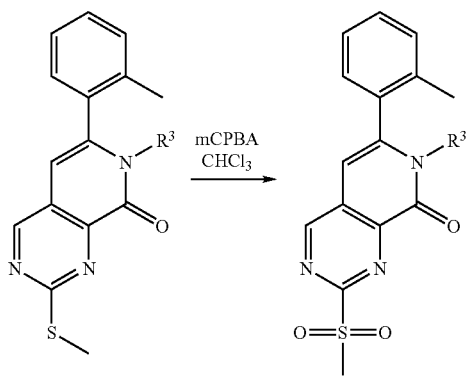

The appropriate lactam (0.7 mmol) (prepared in (E)) was dissolved in chloroform (4 ml). 3-Chloroperoxybenzoic acid (mCPBA) (1.0 mmol) was added and the mixture was stirred at ambient temperature for 1 h. A second portion of 3-chloroperoxybenzoic acid was added and the mixture stirred for a further 18 h. The mixture was poured into saturated aqueous sodium sulfite solution (25 ml) and product was extracted into dichloromethane (2×15 ml). The combined extracts were washed with 2M aqueous sodium carbonate solution (25 ml), then dried (MgSO₄) and evaporated in vacuo. The residual oil was purified by flash column chromatography over silica using dichloromethane as eluant. Appropriate fractions were combined and the solvent removed in vacuo to give the desired sulfone.

Compounds Synthesized:

| Example No | R³ | m/z (MH⁺) | Retention time (minutes) | Purity (%) |
|---|---|---|---|---|
| F1 | —Me | 330 | 3.01 | 100 |
| F2 | propyl-OH | 360 | 2.80 | 60 |
| F3 | butyl-OH | 374 | 2.92 | 66 |
| F4 | propanamide (CH₂CH₂C(O)NH₂) | 387 | 2.77 | 86 |
| F5 | 3-methoxybenzyl | 436 | 3.83 | 74 |

Example G

5-[2-(2-Chloro-phenyl)-2-oxo-ethyl]-2-methylsulfanyl-pyrimidine-4-carboxylic acid amides

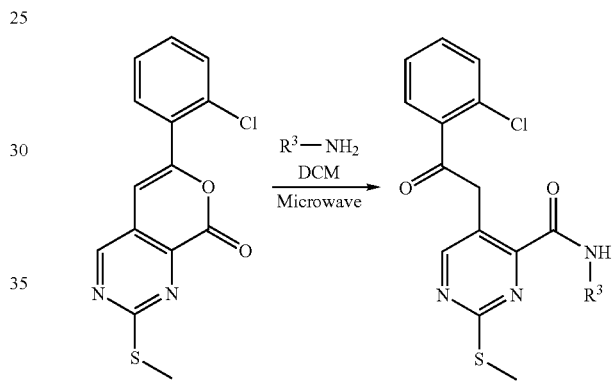

The synthesis was carried out according to the method described in (D) above using 5-(2-chloro-phenylethynyl)-2-methylsulfanyl-pyrimidine-4-carboxylic acid methyl ester and the appropriate amines.

Compounds Synthesized:

| Example No | R³ | m/z (MH⁺) | Retention time (minutes) | Purity (%) |
|---|---|---|---|---|
| G1 | —Me | 336 | 3.46 | 96 |
| G2 | propanamide | 379 | 3.58 | 88 |
| G3 | propyl-OH | 366 | 3.25 | 89 |
| G4 | (1,5-dimethyl-1H-pyrazol-3-yl)ethyl | 430 | 3.61 | 94 |
| G5 | H | 322 | 3.22 | 95 |

-continued

| Example No | R³ | m/z (MH⁺) | Retention time (minutes) | Purity (%) |
|---|---|---|---|---|
| G6 | propanamide (-CH₂CH₂C(O)NH₂) | 379 | 3.58 | 88 |
| G7 | -CH₂CH₂CH₂OH | 380 | 3.29 | 96 |
| G8 | butanamide (-CH₂CH₂CH₂C(O)NH₂) | 393 | 3.19 | 48 |
| G9 | isobutyl | 364 | 3.87 | 81 |
| G10 | 3-methoxybenzyl | 422 | 4.05 | 84 |
| G11 | 5-methyl-pyrazol-3-yl-methyl | 388 | 3.51 | 100 |

Example H 6-(2-Chloro-phenyl)-7-substituted-2-methylsulfanyl-7H-pyrido[3,4-d]pyrimidin-8-ones

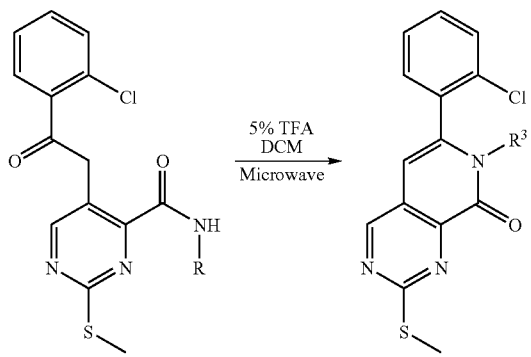

5% TFA DCM Microwave

The synthesis was carried out according to the method described in (E) above using the appropriate amide synthesised in (G).

Compounds Synthesized:

| Example No | R³ | m/z (MH⁺) | Retention time (minutes) | Purity (%) |
|---|---|---|---|---|
| H1 | —Me | 318 | 3.42 | 97 |
| H2 | -CH₂CH₂OH | 348 | 3.21 | 91 |
| H3 | -CH₂C(O)NH₂ (propanamide) | 361 | 3.07 | 88 |
| H4 | (1,5-dimethyl-pyrazol-3-yl)ethyl | 411 | 3.49 | 93 |
| H5 | H | 304 | 3.13 | 97 |
| H6 | -CH₂CH₂CH₂OH | 362 | 3.25 | 80 |
| H7 | -CH₂CH₂CH₂C(O)NH₂ | 375 | 3.05 | 75 |
| H8 | 3-methoxybenzyl | 424 | 3.89 | 84 |
| H9 | tetrahydrofuran-2-ylmethyl | 388 | 3.51 | 93 |

Example I 6-(2-Chloro-phenyl)-2-methanesulfonyl-7-substituted-7H-pyrido[3,4-d]pyrimidin-8-ones

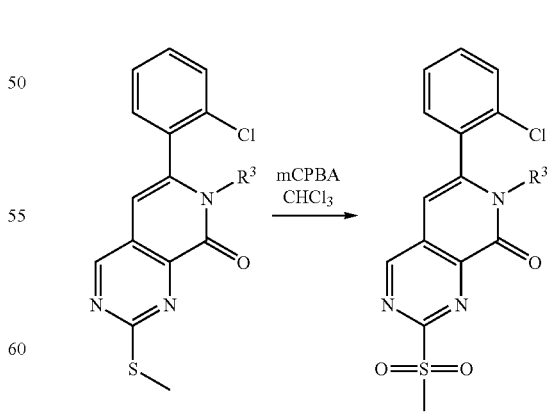

mCPBA CHCl₃

The synthesis was carried out according to the method described in (F) above using the appropriate lactam synthesised in (H).

Compounds Synthesized:

| Example No | R³ | m/z (MH⁺) | Retention time (minutes) | Purity (%) |
|---|---|---|---|---|
| I1 | —Me | 350 | 3.04 | 100 |
| I2 | propyl-OH | 380 | 2.87 | 100 |
| I3 | propanamide | 393 | 2.72 | 83 |
| I4 | ethyl-(1,5-dimethylpyrazol-3-yl) | 444 | 3.22 | 80 |
| I5 | H | 336 | 2.21 | 83 |
| I6 | butyl-OH | 394 | 2.93 | 73 |
| I7 | ethyl-(3-methoxyphenyl) | 456 | 3.59 | 89 |
| I8 | ethyl-(tetrahydrofuran-2-yl) | 420 | 3.29 | 80 |

Synthesis of Final Products

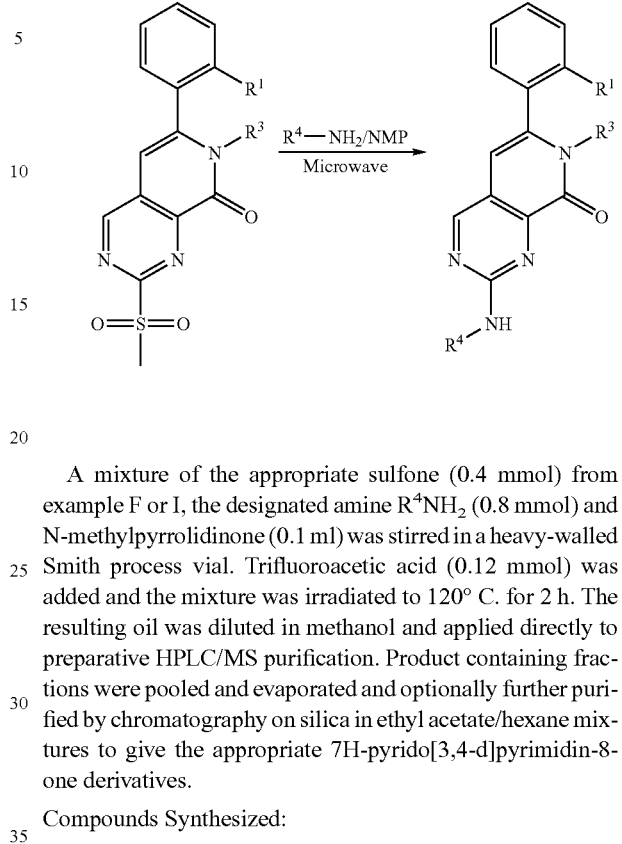

A mixture of the appropriate sulfone (0.4 mmol) from example F or I, the designated amine R⁴NH₂ (0.8 mmol) and N-methylpyrrolidinone (0.1 ml) was stirred in a heavy-walled Smith process vial. Trifluoroacetic acid (0.12 mmol) was added and the mixture was irradiated to 120° C. for 2 h. The resulting oil was diluted in methanol and applied directly to preparative HPLC/MS purification. Product containing fractions were pooled and evaporated and optionally further purified by chromatography on silica in ethyl acetate/hexane mixtures to give the appropriate 7H-pyrido[3,4-d]pyrimidin-8-one derivatives.

Compounds Synthesized:

Examples 1-47

| Example No | Systematic Name | m/z (MH+) | ¹H-NMR |
|---|---|---|---|
| 1 | 7-Methyl-2-(4-morpholin-4-yl-phenylamino)-6-o-tolyl-7H-pyrido[3,4-d]pyrimidin-8-one | 428.1 | 400 MHz, CDCl3: 8.84 (s, 1H); 7.68 (broad s, 1H); 7.62 (broad d, 2H); 7.39 (t, 1H); 7.34-7.28 (m, 2H); 7.23 (d, 1H); 6.97 (broad d, 2H); 6.29 (s, 1H); 3.88 (m, 4H); 3.31 (s, 3H); 3.14 (m, 4H); 2.18 (s, 3H). |
| 2 | 2-(3-Hydroxymethyl-phenylamino)-7-methyl-6-o-tolyl-7H-pyrido[3,4-d]pyrimidin-8-one | | |
| 3 | 7-Methyl-2-[4-(4-methyl-piperazin-1-yl)-phenylamino]-6-o-tolyl-7H-pyrido[3,4-d]pyrimidin-8-one | 441.1 | 400 MHz, DMSOd6: 9.89 (s, 1H); 9.04 (s, 1H); 7.81 (broad d, 2H); 7.47-7.37 (m, 2H); 7.37-7.33 (m, 2H); 6.93 (d, 2H); 6.44 (s, 1H); 3.16 (s, 3H); 3.13-3.07 (m, 4H); 2.27-2.25 (m, 4H); 2.17 (s, 3H). |
| 4 | 2-(2-Hydroxy-1-hydroxymethyl-ethylamino)-7-methyl-6-o-tolyl-7H-pyrido[3,4-d]pyrimidin-8-one | 341.1 | 400 MHz, DMSOd6: 8.92 (s, 1H); 7.45-7.35 (m, 2H); 7.35-7.30 (m, 2H); 7.13 (broad s, 1H); 6.37 (s, 1H); 4.77 (broad s, 2H); 4.11-4.02 (m, 1H); 3.61-3.58 (m, 4H); 3.13 (s, 3H); 2.15 (s, 3H). |
| 5 | 2-{2-[4-(2-Hydroxy-ethylsulfamoyl)-phenylamino]-8-oxo-6-o-tolyl-8H- | 509.5 | |

-continued

| Example No | Systematic Name | m/z (MH+) | ¹H-NMR |
|---|---|---|---|
| | pyrido[3,4-d]pyrimidin-7-yl}-acetamide | | |
| 6 | N-(2-Hydroxy-ethyl)-4-(7-methyl-8-oxo-6-o-tolyl-7,8-dihydro-pyrido[3,4-d]pyrimidin-2-ylamino)-benzenesulfonamide | 466.0 | 400 MHz, DMSOd6: 10.61 (s, 1H); 9.20 (s, 1H); 8.18 (d, 2H); 7.74 (d, 2H); 7.48-7.38 (m, 3H); 7.37-7.35 (m, 2H); 6.53 (s, 1H); 4.66 (t, 1H); 3.37 (q, 2H); 3.20 (s, 3H); 2.80 (q, 2H); 2.18 (s, 3H). |
| 7 | 2-[4-(2-Diethylamino-ethoxy)-phenylamino]-7-methyl-6-o-tolyl-7H-pyrido[3,4-d]pyrimidin-8-one | 458.1 | |
| 8 | 2-[2-(3-Methanesulfinyl-phenylamino)-8-oxo-6-o-tolyl-8H-pyrido[3,4-d]pyrimidin-7-yl]-acetamide | 448.2 | |
| 9 | 2-[8-Oxo-2-(tetrahydro-pyran-4-ylamino)-6-o-tolyl-8H-pyrido[3,4-d]pyrimidin-7-yl]-acetamide | 394.0 | |
| 10 | 2-(3-Methanesulfinyl-phenylamino)-7-methyl-6-o-tolyl-7H-pyrido[3,4-d]pyrimidin-8-one | 405.0 | |
| 11 | 7-(1,5-Dimethyl-1H-pyrazol-3-ylmethyl)-2-(4-morpholin-4-yl-phenylamino)-6-o-tolyl-7H-pyrido[3,4-d]pyrimidin-8-one | 522.2 | |
| 12 | 7-Methyl-2-(tetrahydro-pyran-4-ylamino)-6-o-tolyl-7H-pyrido[3,4-d]pyrimidin-8-one | 351.1 | |
| 13 | 7-(1,5-Dimethyl-1H-pyrazol-3-ylmethyl)-2-(2-hydroxy-1-hydroxymethyl-ethylamino)-6-o-tolyl-7H-pyrido[3,4-d]pyrimidin-8-one | 435.1 | |
| 14 | 7-(1,5-Dimethyl-1H-pyrazol-3-ylmethyl)-2-(tetrahydro-pyran-4-ylamino)-6-o-tolyl-7H-pyrido[3,4-d]pyrimidin-8-one | 445.2 | |
| 15 | 7-(3-Hydroxy-propyl)-2-[4-(4-methyl-piperazin-1-yl)-phenylamino]-6-o-tolyl-7H-pyrido[3,4-d]pyrimidin-8-one | 485.5 | |
| 16 | N-(2-Hydroxy-ethyl)-4-[7-(3-hydroxy-propyl)-8-oxo-6-o-tolyl-7,8-dihydro-pyrido[3,4-d]pyrimidin-2-ylamino]-benzenesulfonamide | 510.1 | |

-continued

| Example No | Systematic Name | m/z (MH+) | ¹H-NMR |
|---|---|---|---|
| 17 | 2-[4-(2-Diethylamino-ethoxy)-phenylamino]-7-(3-hydroxy-propyl)-6-o-tolyl-7H-pyrido[3,4-d]pyrimidin-8-one | 502.2 | |
| 18 | 7-(3-Hydroxy-propyl)-2-(3-methanesulfinyl-phenylamino)-6-o-tolyl-7H-pyrido[3,4-d]pyrimidin-8-one | 449.1 | |
| 19 | 7-(3-Hydroxy-propyl)-2-(tetrahydro-pyran-4-ylamino)-6-o-tolyl-7H-pyrido[3,4-d]pyrimidin-8-one | 395.3 | 400 MHz, DMSOd6: 8.91 (s, 1H); 7.46-7.29 (m, 5H); 6.32 (s, 1H); 4.35-4.29 (m, 1H); 4.14-4.01 (m, 2H); 3.94-3.86 (m, 2H); 3.42 (broad t, 2H); 3.22-3.12 (m, 2H); 2.13 (s, 3H); 1.93-1.82 (m, 2H); 1.68-1.44 (m, 4H). |
| 20 | 7-(3-Methoxy-benzyl)-2-[4-(4-methyl-piperazin-1-yl)-phenylamino]-6-o-tolyl-7H-pyrido[3,4-d]pyrimidin-8-one | 547.5 | |
| 21 | N-(2-Hydroxy-ethyl)-4-[7-(3-methoxy-benzyl)-8-oxo-6-o-tolyl-7,8-dihydro-pyrido[3,4-d]pyrimidin-2-ylamino]-benzenesulfonamide | 572.4 | |
| 22 | 2-[4-(2-Diethylamino-ethoxy)-phenylamino]-7-(3-methoxy-benzyl)-6-o-tolyl-7H-pyrido[3,4-d]pyrimidin-8-one | 564.5 | |
| 23 | 2-(3-Methanesulfinyl-phenylamino)-7-(3-methoxy-benzyl)-6-o-tolyl-7H-pyrido[3,4-d]pyrimidin-8-one | 511.2 | |
| 24 | 7-(3-Methoxy-benzyl)-2-(tetrahydro-pyran-4-ylamino)-6-o-tolyl-7H-pyrido[3,4-d]pyrimidin-8-one | 457.3 | |
| 25 | 3-[2-(3-Hydroxymethyl-phenylamino)-8-oxo-6-o-tolyl-8H-pyrido[3,4-d]pyrimidin-7-yl]-propionamide | | |
| 26 | 3-{2-[4-(2-Hydroxy-ethylsulfamoyl)-phenylamino]-8-oxo-6-o-tolyl-8H-pyrido[3,4-d]pyrimidin-7-yl}-propionamide | | |
| 27 | 3-[2-(3-Methanesulfinyl-phenylamino)-8-oxo-6-o-tolyl-8H-pyrido[3,4-d]pyrimidin-7-yl]-propionamide | | |

-continued

| Example No | Systematic Name | m/z (MH+) | ¹H-NMR |
|---|---|---|---|
| 28 | 3-[8-Oxo-2-(tetrahydro-pyran-4-ylamino)-6-o-tolyl-8H-pyrido[3,4-d]pyrimidin-7-yl]-propionamide | | |
| 29 | 2-[6-(2-Chloro-phenyl)-8-oxo-2-(tetrahydro-pyran-4-ylamino)-8H-pyrido[3,4-d]pyrimidin-7-yl]-acetamide | | 400 MHz, CDCl3: 8.77 (s, 1H); 7.54-7.34 (m, 4H); 6.34 (s, 1H); 6.06 (broad s, 1H); 5.38 (broad s, 1H); 4.98 (d, 1H); 4.26 (broad s, 1H); 4.04-3.95 (m, 3H); 3.63-3.53 (m, 3H); 2.13-2.02 (m, 2H); 1.60 (dq, 2H). |
| 30 | 6-(2-Chloro-phenyl)-7-(1,5-dimethyl-1H-pyrazol-3-ylmethyl)-2-[4-(4-methyl-piperazin-1-yl)-phenylamino]-7H-pyrido[3,4-d]pyrimidin-8-one | | |
| 31 | 6-(2-Chloro-phenyl)-2-[4-(2-diethylamino-ethoxy)-phenylamino]-7-(1,5-dimethyl-1H-pyrazol-3-ylmethyl)-7H-pyrido[3,4-d]pyrimidin-8-one | | |
| 32 | 6-(2-Chloro-phenyl)-7-(1,5-dimethyl-1H-pyrazol-3-ylmethyl)-2-(tetrahydro-pyran-4-ylamino)-7H-pyrido[3,4-d]pyrimidin-8-one | 465.3 | |
| 33 | 6-(2-Chloro-phenyl)-7-(1,5-dimethyl-1H-pyrazol-3-ylmethyl)-2-(3-methanesulfinyl-phenylamino)-7H-pyrido[3,4-d]pyrimidin-8-one | 519.0 | 400 MHz, CDCl3: 9.12 (s, 1H); 8.17 (s, 1H); 7.87-7.89 (m, 1H); 7.59-7.36 (m, 5H); 7.35-7.22 (m, 1H); 6.53 (s, 1H); 6.14 (s, 1H); 5.47 (d, 1H); 4.78 (d, 1H); 3.92 (s, 3H); 2.80 (s, 3H); 2.28 (s, 3H). |
| 34 | 6-(2-Chloro-phenyl)-7-(3-hydroxy-propyl)-2-[4-(4-methyl-piperazin-1-yl)-phenylamino]-7H-pyrido[3,4-d]pyrimidin-8-one | | |
| 35 | 6-(2-Chloro-phenyl)-7-(3-hydroxy-propyl)-2-(tetrahydro-pyran-4-ylamino)-7H-pyrido[3,4-d]pyrimidin-8-one | | |
| 36 | 6-(2-Chloro-phenyl)-7-(3-methoxy-benzyl)-2-[4-(4-methyl-piperazin-1-yl)-phenylamino]-7H-pyrido[3,4-d]pyrimidin-8-one | | |
| 37 | 4-[6-(2-Chloro-phenyl)-7-(3-methoxy-benzyl)-8-oxo-7,8-dihydro-pyrido[3,4-d]pyrimidin-2- | | |

-continued

| Example No | Systematic Name | m/z (MH+) | ¹H-NMR |
|---|---|---|---|
| | ylamino]-N-(2-hydroxy-ethyl)-benzenesulfonamide | | |
| 38 | 6-(2-Chloro-phenyl)-2-[4-(2-diethylamino-ethoxy)-phenylamino]-7-(3-methoxy-benzyl)-7H-pyrido[3,4-d]pyrimidin-8-one | | |
| 39 | 6-(2-Chloro-phenyl)-2-(3-methanesulfinyl-phenylamino)-7-(3-methoxy-benzyl)-7H-pyrido[3,4-d]pyrimidin-8-one | | |
| 40 | 6-(2-Chloro-phenyl)-7-(3-methoxy-benzyl)-2-(tetrahydro-pyran-4-ylamino)-7H-pyrido[3,4-d]pyrimidin-8-one | | |
| 41 | 6-(2-Chloro-phenyl)-2-(3-hydroxymethyl-phenylamino)-7-(tetrahydro-furan-2-ylmethyl)-7H-pyrido[3,4-d]pyrimidin-8-one | | |
| 42 | 6-(2-Chloro-phenyl)-2-[4-(4-methyl-piperazin-1-yl)-phenylamino]-7-(tetrahydro-furan-2-ylmethyl)-7H-pyrido[3,4-d]pyrimidin-8-one | | |
| 43 | 4-[6-(2-Chloro-phenyl)-8-oxo-7-(tetrahydro-furan-2-ylmethyl)-7,8-dihydro-pyrido[3,4-d]pyrimidin-2-ylamino]-N-(2-hydroxy-ethyl)-benzenesulfonamide | | |
| 44 | 6-(2-Chloro-phenyl)-2-[4-(2-diethylamino-ethoxy)-phenylamino]-7-(tetrahydro-furan-2-ylmethyl)-7H-pyrido[3,4-d]pyrimidin-8-one | | |
| 45 | 6-(2-Chloro-phenyl)-2-(3-methanesulfinyl-phenylamino)-7-(tetrahydro-furan-2-ylmethyl)-7H-pyrido[3,4-d]pyrimidin-8-one | | |
| 46 | 6-(2-Chloro-phenyl)-7-(tetrahydro-furan-2-ylmethyl)-2-(tetrahydro-pyran-4-ylamino)-7H-pyrido[3,4-d]pyrimidin-8-one | | |
| 47 | 3-[6-(2-Chloro-phenyl)-2-(2- | | |

-continued

| Example No | Systematic Name | m/z (MH+) | ¹H-NMR |
|---|---|---|---|
| | hydroxy-1-hydroxymethyl-ethylamino)-8-oxo-8H-pyrido[3,4-d]pyrimidin-7-yl]-propionamide | | |

The invention claimed is:

1. A compound according to formula I,

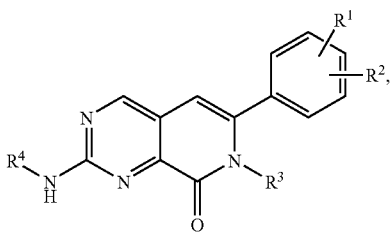

formula I wherein

R¹ is selected from the group consisting of: halogen, alkyl, alkoxy, halogenated alkyl and halogenated alkoxy;

R² is selected from the group consisting of: hydrogen, halogen, alkyl, alkoxy, halogenated alkyl and halogenated alkoxy;

R³ is alkyl which is optionally substituted one or several times with cyano, —OR, —NRR', —C(O)NRR', —NR—C(O)-alkyl, —S(O)₂NRR', —NR—S(O)₂-alkyl, heteroaryl, heterocyclyl, unsubstituted phenyl or phenyl substituted one or several times with halogen, alkyl, alkoxy or cyano;

R⁴ is selected from the group consisting of:
   a) alkyl wherein the alkyl is optionally substituted one or several times with —OR or —NRR';
   b) phenyl wherein the phenyl is optionally substituted one or several times with alkyl, alkoxy, heterocyclyl, —C(O)NRR', —NR—C(O)-alkyl, —S(O)-alkyl, —S(O)₂NR-alkyl or —NR—S(O)₂-alkyl, and wherein all alkyl and alkoxy groups are optionally substituted one or several times with —OR or —NRR'; and
   c) heterocyclyl; and R and R' are each independently hydrogen or alkyl;

or a pharmaceutically-acceptable salt thereof.

2. A compound according to claim 1, wherein

R¹ is halogen or alkyl;

R² is hydrogen;

R³ is alkyl which is optionally substituted one or several times with —OR, —C(O)NRR', heteroaryl, heterocyclyl, unsubstituted phenyl or phenyl substituted one or several times with alkoxy; and R⁴ is selected from the group consisting of:
   a) alkyl wherein the alkyl is optionally substituted one or several times with —OR or —NRR';
   b) phenyl wherein the phenyl is optionally substituted one or several times with alkyl, alkoxy, heterocyclyl, —S(O)-alkyl or —S(O)₂NR-alkyl, and wherein all alkyl and alkoxy groups are optionally substituted one or several times with —OR or —NRR'; and
   c) heterocyclyl.

3. A compound according to claim 1, wherein

R⁴ is selected from the group consisting of:
   a) alkyl wherein the alkyl is optionally substituted one or several times with —OR or —NRR'; and
   b) heterocyclyl.

4. A compound according to claim 1, wherein

R⁴ is phenyl optionally substituted one or several times with alkyl, alkoxy, heterocyclyl, —S(O)-alkyl or —S(O)₂NR-alkyl, and wherein all alkyl and alkoxy groups are optionally substituted one or several times with —OR or —NRR'.

5. A compound according to claim 1, selected from the group consisting of:

2-(2-Hydroxy-1-hydroxymethyl-ethylamino)-7-methyl-6-o-tolyl-7H-pyrido[3,4-d]pyrimidin-8-one;

7-(1,5-Dimethyl-1H-pyrazol-3-ylmethyl)-2-(2-hydroxy-1-hydroxymethyl-ethylamino)-6-o-tolyl-7H-pyrido[3,4-d]pyrimidin-8-one;

3-[6-(2-Chloro-phenyl)-2-(2-hydroxy-1-hydroxymethyl-ethylamino)-8-oxo-8H-pyrido[3,4-d]pyrimidin-7-yl]-propionamide;

7-Methyl-2-(4-morpholin-4-yl-phenylamino)-6-o-tolyl-7H-pyrido[3,4-d]pyrimidin-8-one;

2-(3-Hydroxymethyl-phenylamino)-7-methyl-6-o-tolyl-7H-pyrido[3,4-d]pyrimidin-8-one;

7-Methyl-2-[4-(4-methyl-piperazin-1-yl)-phenylamino]-6-o-tolyl-7H-pyrido[3,4-d]pyrimidin-8-one;

2-{2-[4-(2-Hydroxy-ethylsulfamoyl)-phenylamino]-8-oxo-6-o-tolyl-8H-pyrido[3,4-d]pyrimidin-7-yl}-acetamide;

N-(2-Hydroxy-ethyl)-4-(7-methyl-8-oxo-6-o-tolyl-7,8-dihydro-pyrido[3,4-d]pyrimidin-2-ylamino)-benzenesulfonamide;

2-[4-(2-Diethylamino-ethoxy)-phenylamino]-7-methyl-6-o-tolyl-7H-pyrido[3,4-d]pyrimidin-8-one;

2-[2-(3-Methanesulfinyl-phenylamino)-8-oxo-6-o-tolyl-8H-pyrido[3,4-d]pyrimidin-7-yl]-acetamide;

2-(3-Methanesulfinyl-phenylamino)-7-methyl-6-o-tolyl-7H-pyrido[3,4-d]pyrimidin-8-one;

7-(1,5-Dimethyl-1H-pyrazol-3-ylmethyl)-2-(4-morpholin-4-yl-phenylamino)-6-o-tolyl-7H-pyrido[3,4-d]pyrimidin-8-one;

7-(3-Hydroxy-propyl)-2-[4-(4-methyl-piperazin-1-yl)-phenylamino]-6-o-tolyl-7H-pyrido[3,4-d]pyrimidin-8-one;

N-(2-Hydroxy-ethyl)-4-[7-(3-hydroxy-propyl)-8-oxo-6-o-tolyl-7,8-dihydro-pyrido[3,4-d]pyrimidin-2-ylamino]-benzenesulfonamide;

2-[4-(2-Diethylamino-ethoxy)-phenylamino]-7-(3-hydroxy-propyl)-6-o-tolyl-7H-pyrido[3,4-d]pyrimidin-8-one;

7-(3-Hydroxy-propyl)-2-(3-methanesulfinyl-phenylamino)-6-o-tolyl-7H-pyrido[3,4-d]pyrimidin-8-one;

7-(3-Methoxy-benzyl)-2-[4-(4-methyl-piperazin-1-yl)-phenylamino]-6-o-tolyl-7H-pyrido[3,4-d]pyrimidin-8-one;

N-(2-Hydroxy-ethyl)-4-[7-(3-methoxy-benzyl)-8-oxo-6-o-tolyl-7,8-dihydro-pyrido[3,4-d]pyrimidin-2-ylamino]-benzenesulfonamide;

2-[4-(2-Diethylamino-ethoxy)-phenylamino]-7-(3-methoxy-benzyl)-6-o-tolyl-7H-pyrido[3,4-d]pyrimidin-8-one;

2-(3-Methanesulfinyl-phenylamino)-7-(3-methoxy-benzyl)-6-o-tolyl-7H-pyrido[3,4-d]pyrimidin-8-one;

3-[2-(3-Hydroxymethyl-phenylamino)-8-oxo-6-o-tolyl-8H-pyrido[3,4-d]pyrimidin-7-yl]-propionamide;

3-{2-[4-(2-Hydroxy-ethylsulfamoyl)-phenylamino]-8-oxo-6-o-tolyl-8H-pyrido[3,4-d]pyrimidin-7-yl}-propionamide;

3-[2-(3-Methanesulfinyl-phenylamino)-8-oxo-6-o-tolyl-8H-pyrido[3,4-d]pyrimidin-7-yl]-propionamide;

6-(2-Chloro-phenyl)-7-(1,5-dimethyl-1H-pyrazol-3-ylmethyl)-2-[4-(4-methyl-piperazin-1-yl)-phenylamino]-7H-pyrido[3,4-d]pyrimidin-8-one;

6-(2-Chloro-phenyl)-2-[4-(2-diethylamino-ethoxy)-phenylamino]-7-(1,5-dimethyl-1H-pyrazol-3-ylmethyl)-7H-pyrido[3,4-d]pyrimidin-8-one;

6-(2-Chloro-phenyl)-7-(1,5-dimethyl-1H-pyrazol-3-ylmethyl)-2-(3-methanesulfinyl-phenylamino)-7H-pyrido[3,4-d]pyrimidin-8-one;

6-(2-Chloro-phenyl)-7-(3-hydroxy-propyl)-2-[4-(4-methyl-piperazin-1-yl)-phenylamino]-7H-pyrido[3,4-d]pyrimidin-8-one;

6-(2-Chloro-phenyl)-7-(3-methoxy-benzyl)-2-[4-(4-methyl-piperazin-1-yl)-phenylamino]-7H-pyrido[3,4-d]pyrimidin-8-one;

4-[6-(2-Chloro-phenyl)-7-(3-methoxy-benzyl)-8-oxo-7,8-dihydro-pyrido[3,4-d]pyrimidin-2-ylamino]-N-(2-hydroxy-ethyl)-benzenesulfonamide;

6-(2-Chloro-phenyl)-2-[4-(2-diethylamino-ethoxy)-phenylamino]-7-(3-methoxy-benzyl)-7H-pyrido[3,4-d]pyrimidin-8-one;

6-(2-Chloro-phenyl)-2-(3-methanesulfinyl-phenylamino)-7-(3-methoxy-benzyl)-7H-pyrido[3,4-d]pyrimidin-8-one;

6-(2-Chloro-phenyl)-2-(3-hydroxymethyl-phenylamino)-7-(tetrahydro-furan-2-ylmethyl)-7H-pyrido[3,4-d]pyrimidin-8-one;

6-(2-Chloro-phenyl)-2-[4-(4-methyl-piperazin-1-yl)-phenylamino]-7-(tetrahydro-furan-2-ylmethyl)-7H-pyrido[3,4-d]pyrimidin-8-one;

4-[6-(2-Chloro-phenyl)-8-oxo-7-(tetrahydro-furan-2-ylmethyl)-7,8-dihydro-pyrido[3,4-d]pyrimidin-2-ylamino]-N-(2-hydroxy-ethyl)-benzenesulfonamide;

6-(2-Chloro-phenyl)-2-[4-(2-diethylamino-ethoxy)-phenylamino]-7-(tetrahydro-furan-2-ylmethyl)-7H-pyrido[3,4-d]pyrimidin-8-one;

6-(2-Chloro-phenyl)-2-(3-methanesulfinyl-phenylamino)-7-(tetrahydro-furan-2-ylmethyl)-7H-pyrido[3,4-d]pyrimidin-8-one;

2-[8-oxo-2-(tetrahydro-pyran-4-ylamino)-6-o-tolyl-8H-pyrido[3,4-d]pyrimidin-7-yl]-acetamide;

7-Methyl-2-(tetrahydro-pyran-4-ylamino)-6-o-tolyl-7H-pyrido[3,4-d]pyrimidin-8-one;

7-(1,5-Dimethyl-1H-pyrazol-3-ylmethyl)-2-(tetrahydro-pyran-4-ylamino)-6-o-tolyl-7H-pyrido[3,4-d]pyrimidin-8-one;

7-(3-Hydroxy-propyl)-2-(tetrahydro-pyran-4-ylamino)-6-o-tolyl-7H-pyrido[3,4-d]pyrimidin-8-one;

7-(3-Methoxy-benzyl)-2-(tetrahydro-pyran-4-ylamino)-6-o-tolyl-7H-pyrido[3,4-d]pyrimidin-8-one;

3-[8-oxo-2-(tetrahydro-pyran-4-ylamino)-6-o-tolyl-8H-pyrido[3,4-d]pyrimidin-7-yl]-propionamide;

2-[6-(2-Chloro-phenyl)-8-oxo-2-(tetrahydro-pyran-4-ylamino)-8H-pyrido[3,4-d]pyrimidin-7-yl]-acetamide;

6-(2-Chloro-phenyl)-7-(1,5-dimethyl-1H-pyrazol-3-ylmethyl)-2-(tetrahydro-pyran-4-ylamino)-7H-pyrido[3,4-d]pyrimidin-8-one;

6-(2-Chloro-phenyl)-7-(3-hydroxy-propyl)-2-(tetrahydro-pyran-4-ylamino)-7H-pyrido[3,4-d]pyrimidin-8-one;

6-(2-Chloro-phenyl)-7-(3-methoxy-benzyl)-2-(tetrahydro-pyran-4-ylamino)-7H-pyrido[3,4-d]pyrimidin-8-one; and 6-(2-Chloro-phenyl)-7-(tetrahydro-furan-2-ylmethyl)-2-(tetrahydro-pyran-4-ylamino)-7H-pyrido[3,4-d]pyrimidin-8-one.

6. A pharmaceutical composition comprising a compound according to claim 1 and a pharmaceutically-acceptable adjuvant.

* * * * *